(12) United States Patent
Wiedmann et al.

(10) Patent No.: US 9,492,367 B2
(45) Date of Patent: Nov. 15, 2016

(54) MIXTURE OF FRAGRANCE COMPOUNDS

(75) Inventors: Wilhelm Wiedmann, Bevern (DE);
Marcus Betzer, Holzminden (DE);
Susanne Borchert, Holzminden (DE);
Stefan Lambrecht, Hehlen (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 13/877,014

(22) PCT Filed: Oct. 5, 2010

(86) PCT No.: PCT/EP2010/064855
§ 371 (c)(1),
(2), (4) Date: Mar. 29, 2013

(87) PCT Pub. No.: WO2010/142815
PCT Pub. Date: Dec. 16, 2010

(65) Prior Publication Data
US 2013/0236402 A1 Sep. 12, 2013

(51) Int. Cl.
| | | |
|---|---|---|
| A61K 8/49 | (2006.01) | |
| A61Q 13/00 | (2006.01) | |
| A61Q 15/00 | (2006.01) | |
| C11B 9/00 | (2006.01) | |
| A61K 8/33 | (2006.01) | |
| A61K 8/34 | (2006.01) | |
| A61Q 17/04 | (2006.01) | |
| C11D 3/50 | (2006.01) | |

(52) U.S. Cl.
CPC .............. *A61K 8/498* (2013.01); *A61K 8/33* (2013.01); *A61K 8/34* (2013.01); *A61K 8/4926* (2013.01); *A61K 8/4973* (2013.01); *A61Q 13/00* (2013.01); *A61Q 15/00* (2013.01); *A61Q 17/04* (2013.01); *C11B 9/0042* (2013.01); *C11B 9/0061* (2013.01); *C11D 3/50* (2013.01)

(58) Field of Classification Search
None
See application file for complete search history.

(56) References Cited

U.S. PATENT DOCUMENTS 3,496,193 A * 2/1970 Heywood et al. ............ 549/359
4,814,322 A * 3/1989 Exner et al. .................. 512/25
5,739,100 A * 4/1998 Horino et al. ................. 512/25
6,297,211 B1 * 10/2001 Frater et al. ................... 512/25
2007/0191258 A1 * 8/2007 Dilk et al. ...................... 512/1

FOREIGN PATENT DOCUMENTS

| DE | 102009001569 A1 | 9/2010 |
|---|---|---|
| EP | 2031047 A1 | 3/2009 |
| WO | WO-2006003053 A1 | 1/2006 |
| WO | WO-2010091969 A1 | 8/2010 |

OTHER PUBLICATIONS

Symrise, manjantol.*
Symrise, magnolan.*
BASF, hydroxycintronellal.*
Panda, Perfume flavors teachnology handbook, Asia Pacific Bussiness Press Inc., India, 2010, Chapter 2, pp. 40-41, published on Oct. 4, 2010.*
Sell Ed. the Chemistry of Fragrances: From Perfumer to Consumer, The royal Society of Chemistry, Cambridge, 2006, Chapter 4, Ingredients for the modern perfumery industry, p. 52.*
International Search Report and Written Opinion Under Rule 43 PCT, International Application No. PCT/EP2010/064855.

* cited by examiner

*Primary Examiner* — Bethany Barham
*Assistant Examiner* — Ping Cao
(74) *Attorney, Agent, or Firm* — Dilworth & Barrese LLP

(57) ABSTRACT

The present invention relates to a mixture comprising or consisting of
a) 2,2-Dimethyl-3-(3-methylphenyl)-propanol (Majantol)
b) 4,4a,5,9b-Tetrahydro-2,4-dimethylindenol[1,2-d]-m-dioxin (Magnolan) and optionally, one, two, three or all of the compounds selected from the group consisting of:
c) 2-Isobutyl-4-methyltetrahydro-2H-pyran-4-ol (Florosa)
d) Citronellyloxyacetaldehyde (Mugenal)
e) 4-n-decylpyridine (Symmarine)
f) 4-(4-methyl-3-penten-1-yl)-3-cyclohexene carboxaldehyde (Vertomugal),
to a fragrance composition containing an organoleptically effective amount of said mixture and to a perfumed product containing said mixture or said fragrance composition and to a method of imparting an odor to a product or enhancing an odor of a product by adding to the product or incorporating into the product an organoleptically effective amount of a mixture or a fragrance composition according to the invention.

21 Claims, No Drawings

MIXTURE OF FRAGRANCE COMPOUNDS

CROSS-REFERENCE TO RELATED APPLICATIONS

This application is a national stage application (under 35 U.S.C. §371) of PCT/EP2010/064855, filed Oct. 5, 2010, the entire contents of which is hereby incorporated by reference.

This invention relates to (i) a mixture of fragrance compounds, to (ii) a fragrance composition containing an organoleptically effective amount of said mixture and to (iii) a perfumed product containing said mixture or said fragrance composition and to (iv) a method of imparting an odor to a product or enhancing an odor of a product by adding to the product or incorporating into the product an organoleptically effective amount of a mixture or a fragrance composition according to the invention.

p-tert.-butyl-alpha-methyldihydrocinnamaldehyde, CAS No. 80-54-6, (also known by its trade-name "Lilial") is a commonly used synthetic fragrance compound. The olfactory properties i.e. the odor of p-tert.-butyl-alpha-methyldihydrocinnamaldehyde is described by the expert as comprising the following olfactory aspects:
white blossom (lilac, lily of the valley)
floral
powdery
crème-like
cosmetically
fresh (resemblance of fresh laundry)
aldehyde-like
warm
dry
soft
hot-iron-like (thus conveying the impression of freshly ironed laundry)

Especially the powdery aspect which is well balanced, harmonic and round-off distinguishes p-tert.-butyl-alpha-methyldihydrocinnamaldehyde from other fragrance compounds or fragrance mixtures and is hardly met by other fragrance compounds or fragrance mixtures. Indeed skilled persons consider the powdery aspect of p-tert.-butyl-alpha-methyldihydrocinnamaldehyde as nearly inimitable.

Moreover, p-tert.-butyl-alpha-methyldihydrocinnamaldehyde distinguishes from many other fragrance compounds or mixtures in terms of its application properties, especially in terms of substantivity and diffusivity. The term "substantivity" describes the capability of a fragrance compound or a fragrance mixture to adhere to a surface. The term "diffusivity" describes the capability of a fragrance compound or a fragrance mixture to disperse within space. p-tert.-butyl-alpha-methyldihydrocinnamaldehyde is known to have a tight adherence to fibers which renders it suitable for imparting a fragrance to textiles, like laundry etc.

The "diffusivity value" gives an idea of the radiation and impact of a material over a distance. The higher the diffusivity value, the faster and stronger the material is perceived. A scale from 1 to 9 is defined wherein 1=no impact within 3 min and 9=high impact within 10 seconds.

Substantivity is an important factor in the persistence of e.g. a fragrance on the skin, a fragrance in shampoos or conditioners on the hair or a fragrance in a detergent or fabric softener on textile fibres. Less substantive compositions would require a higher amount of fragrance compounds, in order to remain effective for an equal period, but this could lead to too high a concentration of fragrance compounds, resulting in a less pleasant odour. Substantivity of a compound is a term used in relation to the degree of the attractive and repulsive forces between said compound and the solid support or substrate upon which it has been deposited. The degree of substantivity is affected by the way in which the fragrance is delivered to the surface, e.g. in a washing/laundering process. This delivery can give rise to extra barriers. The degree of substantivity of a compound depends on both the capability of the compound to cross delivery barriers and how well the compound retains on a substrate after delivery. The latter effect, referred to as retention, is sometimes also used to indicate how well a fragrance compound sticks to a substrate, but retention only relates to the behaviour of a fragrance compound after it has successfully adhered to the substrate. In contrast to substantivity, retention does not include an indication of how well the delivery barriers are crossed by a fragrance compound or mixture. Hence, a compound may—despite a good retention—be a poor fragrance compound in e.g. a personal care product, or a washing or laundering product if it does not manage to cross the barrier from product to substrate sufficiently, i.e. if it has too low a substantivity. Examples of applications in which a fragrance compound or mixture has to take such barriers are the washing of laundry, hair, skin or surfaces. This involves transfer from an aqueous detergent solution or dispersion to a substrate, such as skin, hair, a textile, a ceramic or a surface. The nature of a substrate also influences substantivity; under comparable conditions of application, fragrance compounds are in general a lot less substantive on nylon than on wool; cotton occupies an intermediate position. Substantivity can further be complicated by several factors, including temperature during washing and thereafter, pH value and the presence of other compounds.

p-tert.-butyl-alpha-methyldihydrocinnamaldehyde is characterized by a diffusivity value of 6.1 and a substantivity value of 4.

However, recently p-tert.-butyl-alpha-methyldihydrocinnamaldehyde was found to be hazardous to human health. More specifically, p-tert.-butyl-alpha-methyldihydro-cinnamaldehyde is considered to have reprotoxic properties. Furthermore, it was found that p-tert.-butyl-alpha-methyldihydrocinnamaldehyde may act as an allergen and may cause contact dermatitis in susceptible individuals. Therefore, preparations containing more than 5 wt.-% by weight of p-tert.-butyl-alpha-methyldihydrocinnamaldehyde have to be classified and labeled as reprotoxic (R62, possible risk of impaired fertility) according to the current EU regulations 67/548/EEC and 1999/45/EC. Under CLP regulation EC/1272/2008 the threshold for labeling is reduced to 3 wt.-% for reprotoxic effects. Additionally, the International Fragrance Association (IFRA) has established the following limit values for products intended for skin contact:

| category number | category description according to IFRA RIFM QRA Information Booklet | limit value (wt.-%) |
|---|---|---|
| 1 | lip products of all types (solid and liquid lipsticks, balms, etc.) toys | 0.1 |
| 2 | deodorant and antiperspirant products of all types (spray, stick, roll-on, under-arm and body, etc.) | 0.2 |

| category number | category description according to IFRA RIFM QRA Information Booklet) | limit value (wt.-%) |
|---|---|---|
| 3 | hydroalcoholic products applied to recently shaved skin<br>eye products of all types<br>(eye shadow, mascara, eyeliner, eye make-up, eye masks, etc.)<br>men's facial creams, balms<br>tampons<br>baby creams, lotions, oils | 0.6 |
| 4 | hydroalcoholic products applied to unshaved skin (includes body mists: aqueous based, alcoholic based and hydroalcoholic)<br>hair styling aids, hair sprays of all types (pumps, aerosol, etc.)<br>body creams, oils, lotions, fragrancing creams of all types (except baby creams and lotions)<br>ingredients of perfume kits, fragrance compounds for cosmetic kits<br>scent pads, foil packs<br>scent strips for hydroalcoholic products<br>foot care products<br>hair deodorant | 1.9 |
| 5 | women's facial creams/facial make-up<br>hand cream<br>facial masks<br>baby powder and talc<br>hair permanent and other hair chemical treatments (e.g. relaxers) but not hair dyes<br>wipes or refreshing tissues for face, neck, hands, body<br>hand sanitizers | 1.0 |
| 6 | mouthwash, toothpaste | 3.0 |
| 7 | intimate wipes, baby wipes,<br>insect repellent (intended to be applied to the skin) | 0.3 |
| 8 | make-up removers of all types (not including face cleansers)<br>hair styling aids non-spray of all types (mousse, gels, leave-in conditioners, etc.)<br>nail care<br>all powders and talcs (except baby powders and talcs)<br>hair dyes | 2.0 |
| 9 | bar soap (toilet soap)<br>bath gels, foams, mousses, salts, oils and other products added to bathwater<br>body washes (including baby washes) and shower gels of all types<br>conditioner (rinse-off)<br>depilatory<br>face cleansers of all types (washes, gels, scrubs, etc.)<br>facial tissues<br>feminine hygiene - pads, liners<br>liquid soap<br>napkins<br>paper towels<br>shampoos of all types (including baby shampoos)<br>shaving creams of all types (stick, gels, foams, etc.)<br>toilet paper<br>other aerosols (including air fresheners sprays but not including deodorant/antiperspirants, hair styling aids spray | 2.5 |
| 10 | handwash laundry detergents of all types including concentrates<br>fabric softeners of all types including fabric softener sheets<br>other household cleaning products<br>machine wash laundry detergents (liquids, powders, tablets, etc.) including laundry bleaches and concentrates<br>hand dishwashing detergent including concentrates<br>hard surface cleaners of all types (bathroom and kitchen cleansers, furniture polish)<br>diapers<br>shampoos for pets<br>dry cleaning kits<br>toilet seat wipes | 2.5 |

Furthermore, the substance must be stated on the product label of a cosmetic product if used in concentrations above 0.01% by weight in rinse-off products and above 0.001 by weight in leave-on products.

For these reasons the availability of a fragrance substance which imitates and recreates as much as possible of the specific olfactory aspects of p-tert.-butyl-alpha-methyldihydrocinnamaldehyde so that it could replace this compound at least to some extent would be highly desirable and is therefore an important object of the perfume industry. To achieve this object several compounds having a chemical structure similar to that of p-tert.-butyl-alpha-methyldihydrocinnamaldehyde have been tested. Unfortunately compounds having chemical structures similar to that of p-tert.-butyl-alpha-methyldihydrocinnamaldehyde were found to cause similar toxic effects. Therefore, efforts to replace p-tert.-butyl-alpha-methyldihydrocinnamaldehyde by a fragrance compound having a similar chemical structure have not been successful.

WO 2009/027957 discloses perfume raw materials and compositions, which are said to provide the overall performance, including, for example, character and/or odor profiles, of p-tert.-butyl-alpha-methyldihydrocinnamaldehyde. More specifically, 44 perfume raw materials which are said to be useful as core materials that can imitate and recreate the performance of p-tert.-butyl-alpha-methyldihydrocinnamaldehyde in a large number of applications, and 50 perfume raw materials which are said to be useful as supplementary materials when combined with one or more core materials, are disclosed in WO 2009/027957. Additionally, 14 so called cocktails (mixtures of fragrance substances) each comprising up to 10 individual fragrance substances are disclosed. It is rather unlikely that each of the perfume raw materials and fragrance cocktails disclosed in WO 2009/027957 shows the same result when applied in replacement of p-tert.-butyl-alpha-methyldihydrocinnamaldehyde. Thus the skilled person who—based on the teaching of WO 2009/027957—is looking for an adequate replacement of certain olfactory properties of p-tert.-butyl-alpha-methyldihydrocinnamaldehyde must rely on a "trial and error" approach. Taking into account the large variety of perfume raw materials and fragrance cocktails disclosed in WO 2009/027957 such a "trial and error" approach appears to be not very expedient.

Furthermore WO 2009/027957 does not indicate which of the perfume raw materials and fragrance cocktails disclosed therein—if any—are capable of recreating and imitating the powdery aspect of p-tert.-butyl-alpha-methyldihydrocinnamaldehyde which has hitherto been considered as inimitable.

The primary object of the invention was to provide a fragrance substance capable of imitating and recreating at least certain olfactory properties of p-tert.-butyl-alpha-methyldihydrocinnamaldehyde. Moreover, this fragrance substance should have some or all of the above-mentioned technical characteristics and advantages of p-tert.-butyl-alpha-methyldihydrocinnamaldehyde, especially in terms of substantivity and diffusivity. Preferably the fragrance substance should be capable of recreating and imitating the powdery aspect of p-tert.-butyl-alpha-methyldihydrocinnamaldehyde.

To achieve these and other objects the invention provides a mixture consisting of or comprising the compounds listed hereinbelow:
a) 2,2-dimethyl-3-(3-methylphenyl)-propanol (Majantol) CAS-No. 103694-68-4
b) 4,4a,5,9b-tetrahydro-2,4-dimethylindenol[1,2-d]-m-dioxin (Magnolan) CAS-No. 27606-09-3
and optionally, one, two, three or all of the compounds selected from the group consisting of:
c) 2-isobutyl-4-methyltetrahydro-2H-pyran-4-ol (Florosa) CAS-No. 63500-71-0
d) citronellyloxyacetaldehyde (Mugenal) CAS-No. 7492-67-3
e) 4-n-decylpyridine (Symmarine) CAS-No. 1815-99-2
f) 4-(4-methyl-3-penten-1-yl)-3-cyclohexene carboxaldehyde (Vertomugal) CAS-No. 37677-14-8.
(wherein the names given in brackets are trade-names of the above-mentioned compounds).

Surprisingly it was found that a combination of compounds a) and b) and optionally c), d), e) and/or f) is able to imitate and recreate olfactory aspects of p-tert.-butyl-alpha-methyldihydrocinnamaldehyde which are not present in the odor of any of the individual compounds a), b), c), d), e) and f). More specifically a combination of compounds a) and b) and optionally c), d), e) and/or f) imitates and recreates the white lilac blossom aspect of p-tert.-butyl-alpha-methyldihydrocinnamaldehyde, although none of the individual compounds a), b), c), d), e) and f) itself exhibits an odor comprising a white lilac blossom aspect. Furthermore, preferred combinations of compounds a) and b) and—whichever present—c), d), e) and/or f) are capable of recreating and imitating the powdery aspect of p-tert.-butyl-alpha-methyldihydrocinnamaldehyde, although none of the individual compounds a), b), c), d), e) and f) itself exhibits an odor comprising a powdery aspect.

In a mixture of the invention the amounts and/or the ratio of compounds a) and b) and—if present—c), d), e) and/or f) are preferably adjusted in order to optimize the olfactory properties of the mixture. Preferably the amounts and/or the ratio of compounds a) and b)—if present—c), d), e) and/or f) are adjusted so that the mixture provides an odor comprising a white lilac blossom aspect resembling the white lilac blossom aspect of p-tert.-butyl-alpha-methyldihydrocinnamaldehyde. More preferably the amounts and/or the ratio of compounds a) and b) and—if present—c), d), e) and/or f) are adjusted so that the mixture provides an odor comprising a white lilac blossom aspect and a powdery aspect. Most preferably the amounts and the ratio of compounds a), b) and—whichever present—c), d), e) and/or f) are adjusted so that the mixture provides an odor comprising a white lilac blossom aspect and a powdery aspect resembling the powdery aspect of p-tert.-butyl-alpha-methyldihydrocinnamaldehyde.

Preferably a mixture of the invention comprises the compounds a) and b) in a weight ratio in the range of from 1:1 to 100:1, preferably in the range of from 2:1 to 100:1, most preferably in the range from 2:1 to 20:1.

A weight ratio of compounds a) and b) of less than 1.5:1 might result in a predominance of olfactory aspects of compound b) so that the desired olfactory aspects of a combination of compounds a) and b) which imitate and recreate the corresponding olfactory aspects of p-tert.-butyl-alpha-methyldihydrocinnamaldehyde may be suppressed at least to some extent.

On the other hand, a weight ratio of compounds a) and b) of more than 100:1 might result in a predominance of olfactory aspects of compound a) so that the desired olfactory aspects of a combination of compounds a) and b) which imitate and recreate the corresponding olfactory aspects of p-tert.-butyl-alpha-methyldihydrocinnamaldehyde may be suppressed at least to some extent.

More preferably a mixture of the invention consists of or comprises or consists of
34.98-99% by weight, preferably 34.98-98.9% by weight of compound a),
1-30% by weight, preferably 1-25% by weight of compound b),
0-20% by weight, preferably 1-20% by weight of compound c),
0-5%, by weight, preferably 0.1-5% by weight of compound d),
0-0.02% by weight, preferably 0.0001-0.02 by weight % of compound e),
0-35%, preferably 5-30% of compound f),
based on the total amount of compounds a), b), c), d), e) and f) in the mixture.

An amount of any of compounds a), b), c), d), e) and f) above its upper limit given above might result in a predominance of certain olfactory aspects of said compound so that the desired olfactory aspects of a combination of compounds a), b) and—if present—c), d), e) and/or f) which imitate and recreate the corresponding olfactory aspects of p-tert.-butyl-alpha-methyldihydrocinnamaldehyde may be suppressed at least to some extent.

On the other hand, an amount of any of compounds a), b), c), d), e) and f) below its lower limit given above might result in a predominance of the olfactory aspects of any combination of the other compounds or—depending on their amounts and their ratio—of any of the other individual compounds so that the desired olfactory aspects of a combination of compounds a), b), and—if present—c), d), e) and/or f) which imitate and recreate the corresponding properties of p-tert.-butyl-alpha-methyldihydrocinnamaldehyde may be suppressed at least to some extent.

Preferably a mixture of the invention comprises only minor amounts of p-tert.-butyl-alpha-methyldihydrocinnamaldehyde. More preferably a mixture of the invention comprises an amount of p-tert.-butyl-alpha-methyldihydrocinnamaldehyde below 3 wt.-% (but not more than the limit value determined by the IFRA for the respective product category, see table 1), more preferably less than an organoleptically and/or toxicologically effective amount of p-tert.-butyl-alpha-methyldihydrocinnamaldehyde, and especially preferable an amount of p-tert.-butyl-alpha-methyldihydrocinnamaldehyde which is below the limit value which requires declaration of that substance on the product label. Most preferably a mixture of the invention comprises no p-tert.-butyl-alpha-methyldihydrocinnamaldehyde.

A major advantage of the fragrance mixture of the present invention is that none of the compounds a), b), c), d), e) and f) is considered as reprotoxic regarding to current state of knowledge. Furthermore, the olfactory effect which can be achieved by applying p-tert.butyl-alpha-methyldihydrocinnamaldehyde in the allowed concentration range can be enhanced by combining a mixture of the invention with an amount of p-tert.-butyl-alpha-methyldihydrocinnamaldehyde equal to or below the limit values indicated above. Moreover, if declaration of p-tert.-butyl-alpha-methyldihydrocinnamaldehyde is to be avoided, the amount of p-tert.-butyl-alpha-methyldihydrocinnamaldehyde can be reduced to a value below the limit value which requires declaration, and a mixture of the invention can be used to replace the amount of p-tert.-butyl-alpha-methyldihydrocinnamaldehyde which is necessary to obtain the desired olfactory effects.

More preferably, a fragrance mixture of the present invention, is characterized by a diffusivity value in the range of from 5 to 6.5 and/or a substantivity value in the range of from 3 to 5. In especially preferred fragrance mixtures of the invention, the substantivity and/or diffusivity of the fragrance is close to or above that of p-tert.-butyl-alpha-methyldihydrocinnamaldehyde.

A first preferred fragrance mixture of the invention comprises or consists of
a) 2,2-dimethyl-3-(3-methylphenyl)-propanol (Majantol)
b) 4,4a,5,9b-tetrahydro-2,4-dimethylindenol[1,2-d]-m-dioxin (Magnolan)
and preferably none of the compounds c), d), e) and f).

Surprisingly it was found that a combination of compounds a) and b) is able to imitate and recreate the white lilac blossom aspect and some other specific olfactory aspects of p-tert.-butyl-alpha-methyldihydrocinnamaldehyde which are not present in the odor of the individual compounds a) and b).

The olfactory properties of 2,2-dimethyl-3-(3-methylphenyl)-propanol (Majantol, hereinbelow referred to as compound a)) are described by the expert as comprising the following aspects:
white blossom (especially lily of the valley)
floral
fresh
soft.

The olfactory properties of 4,4a,5,9b-tetrahydro-2,4-dimethylindenol[1,2-d]-m-dioxin (Magnolan, hereinbelow referred to as compound b)) are described by the expert as comprising the following aspects:
white blossom (especially white magnolia)
floral (red blossom, peony, geranium)
indol-like.

Combining the compounds a) and b) results in a preferred fragrance mixture having olfactory properties comprising the following aspects:
white blossom (mainly lilac, but also lily of the valley)
floral
fresh
soft
warm
dry.

Thus, a first preferred fragrance mixture of the invention which comprises or consists of the compounds a) and b) is capable of imitating and recreating a wide range of the specific olfactory aspects of p-tert.-butyl-alpha-methyldihydrocinnamaldehyde.

In an above-described first preferred fragrance mixture of the invention the amounts of compounds a) and b) and/or the ratio of compounds a) and b) are preferably adjusted in order to optimize the olfactory properties of the mixture. More preferably the amounts of compounds a) and b) and/or the ratio of compounds a) and b) are adjusted so that the mixture provides an odor comprising a white lilac blossom aspect resembling the white lilac blossom aspect of p-tert.-butyl-alpha-methyldihydrocinnamaldehyde.

Preferably an above-described first preferred fragrance mixture of the invention comprises the compounds a) and b) in a weight ratio in the range of from 2:1 to 100:1, preferably in the range of from 4:1 to 10:1.

More preferably an above-described first preferred fragrance mixture of the invention comprises or consists of
  70-99% by weight, preferably 80-20% by weight of compound a),
  1-30% by weight, preferably 10-20% by weight of compound b),
based on the total amount of compounds a), b), c), d), e) and f) in the mixture.

Further preferably, an above-described first preferred fragrance mixture is a fragrance mixture according to an alternative (i) of the invention. A fragrance mixture according to alternative (i) of the invention comprises or consists of
  70-99% by weight, preferably 80-90% by weight of compound a),
  1-30% by weight, preferably 10-20% by weight of compound b),
  0% by weight of compound c),
  0%, by weight of compound d),
  0% by weight of compound e),
  0% by weight of compound f),
based on the total amount of compounds a), b), c), d), e) and f) in the mixture.

An amount of compound a) of less than 70% and, accordingly an amount of compound b) of more than 30% might result in a predominance of olfactory aspects of compound b) so that the desired olfactory aspects of a combination of compounds a) and b), especially according to alternative (i) of the invention, which imitate and recreate the corresponding olfactory aspects of p-tert.-butyl-alpha-methyldihydrocinnamaldehyde may be suppressed at least to some extent.

On the other hand an amount of compound a) of more than 99% and, accordingly an amount of compound b) of less than 1% might result in a predominance of olfactory aspects of compound a) so that the desired olfactory aspects of a combination of compounds a) and b), especially according to alternative (i) of the invention, which imitate and recreate the corresponding olfactory aspects of p-tert.-butyl-alpha-methyldihydrocinnamaldehyde may be suppressed at least to some extent.

An above-described first preferred fragrance mixture of the invention, especially according to alternative (i) tightly adheres to all common types of fibers, and the fragrance is stable upon storage of a product, e.g. laundry, to which the mixture was applied. More preferably, an above-described first preferred fragrance mixture of the invention, especially according to alternative (i) is characterized by a diffusivity value in the range of from 5.2 to 5.8 (in particular the value is preferably 5.5) and/or a substantivity value in the range of from 3.0 to 3.4 (in particular the value is preferably 3.2).

A second preferred fragrance mixture of the invention comprises or consists of
a) 2,2-dimethyl-3-(3-methylphenyl)-propanol (Majantol)
b) 4,4a,5,9b-tetrahydro-2,4-dimethylindenol[1,2-d]-m-dioxin (Magnolan), and
c) 2-isobutyl-4-methyltetrahydro-2H-pyran-4-ol (Florosa)
and preferably none of the compounds d), e) and f).

Surprisingly it was found that a combination of compounds a), b) and c) is able to imitate and recreate not only the white lilac blossom aspect but also some other specific olfactory aspects of p-tert.-butyl-alpha-methyldihydrocinnamaldehyde which are not present in the odor of any of the individual compounds a), b) and c). Especially surprisingly a combination of compounds a), b) and c) is capable of imitating and recreating the powdery aspect of p-tert.-butyl-alpha-methyldihydrocinnamaldehyde, although none of the compounds a), b) and c) itself exhibits an odor comprising a powdery aspect.

The olfactory properties of compounds a) and b) are as described above.

The olfactory properties of 2-isobutyl-4-methyltetrahydro-2H-pyran-4-ol (Florosa, hereinbelow referred to as compound c)) are described by the expert as comprising the following aspects:
  white blossom (especially white rose)
  fresh.

Combining the compounds a), b) and c) results in a preferred fragrance mixture having olfactory properties comprising the following aspects:
  white blossom (mainly lilac, but also lily of the valley)
  floral
  fresh
  soft
  warm
  dry
  powdery
  crème-like
  cosmetically.

Thus, a second preferred fragrance mixture of the invention which comprises or consists of the compounds a), b) and c) is capable of imitating and recreating a wide range of the specific olfactory aspects of p-tert.-butyl-alpha-methyldihydro-cinnamaldehyde, including the white lilac blossom aspect, and the powdery aspect which hitherto has been considered as inimitable.

In an above-described second preferred fragrance mixture of the invention the amounts of compounds a), b) and c) and/or their ratio are preferably adjusted in order to optimize the olfactory properties of the mixture. More preferably the amounts of compounds a), b) and c) and/or their ratio are adjusted so that the mixture provides an odor comprising a white lilac blossom aspect resembling the white lilac blossom aspect of p-tert.-butyl-alpha-methyldihydrocinnamaldehyde and a powdery aspect resembling the powdery aspect of p-tert.-butyl-alpha-methyldihydrocinnamaldehyde.

Preferably an above-described second preferred fragrance mixture of the invention comprises the compounds a) and b) in a weight ratio in the range of from 2:1 to 100:1, preferably in the range of from 4:1 to 18:1.

More preferably an above-described second preferred fragrance mixture of the invention comprises or consists of
  55-98% by weight, preferably 65-90% by weight of compound a),
  1-25% by weight, preferably 5-17.5% by weight of compound b),
  1-20% by weight, preferably 5-17.5% by weight of compound c),
based on the total amount of compounds a), b), c), d), e) and f) in the mixture.

Further preferably, an above-described second preferred fragrance mixture is a fragrance mixture according to an alternative (ii) of the invention. A fragrance mixture according to alternative (ii) of the invention comprises or consists of
  55-98% by weight, preferably 65-90% by weight of compound a),
  1-25% by weight, preferably 5-17.5% by weight of compound b),
  1-20% by weight, preferably 5-17.5% by weight of compound c),
  0%, by weight of compound d),
  0% by weight of compound e),
  0% by weight of compound f),
based on the total amount of compounds a), b), c), d), e) and f) in the mixture.

An amount of compound c) of less than 1% and, accordingly a total amount of compounds a) and b) of more than 99% might result in a predominance of olfactory aspects of any combination of compounds a) and b) or—depending on their amounts and their ratio—any of the individual compounds a) and b) so that the desired olfactory aspects of a combination of compounds a), b) and c), especially according to alternative (ii) of the invention, which imitate and recreate the corresponding olfactory aspects of p-tert.-butyl-alpha-methyldihydrocinnamaldehyde may be suppressed at least to some extent.

On the other hand an amount of compound c) of more than 20% and, accordingly a total amount of compounds a) and b) of less than 80% might result in a predominance of olfactory aspects of compound c), e.g. the white rose blossom aspect so that the desired olfactory aspects of a combination of compounds a), b) and c), especially according to alternative (ii) of the invention, which imitate and recreate the corresponding olfactory aspects of p-tert.-butyl-alpha-methyldihydrocinnamaldehyde may be suppressed at least to some extent.

An above described second preferred fragrance mixture of the invention, especially according to alternative (ii), has a substantivity and diffusivity of the fragrance which is typically even stronger than that of an above-described first preferred fragrance mixture of the invention, especially upon storage of laundry to which the mixture was applied. More preferably, an above-described second preferred fragrance mixture of the invention, especially according to alternative (ii) is characterized by a diffusivity value in the range of from 5.1 to 5.7 (in particular the value is preferably 5.4) and/or a substantivity value in the range of from 3.3 to 3.7 (in particular the value is preferably 3.5).

A third preferred fragrance mixture of the invention comprises or consists of a) 2,2-dimethyl-3-(3-methylphenyl)-propanol (Majantol)
b) 4,4a,5,9b-tetrahydro-2,4-dimethylindenol[1,2-d]-m-dioxin (Magnolan)
d) citronellyloxyacetaldehyde (Mugenal)
and preferably none of the compounds c), e) and f).

Surprisingly it was found that a combination of compounds a), b) and d) is able to imitate and recreate not only the white lilac blossom aspect but also some other specific olfactory aspects of p-tert.-butyl-alpha-methyldihydrocinnamaldehyde which are not present in the odor of any of the individual compounds a), b) and d). Especially surprisingly a combination of compounds a), b) and d) is capable of imitating and recreating the fresh laundry aspect and the powdery aspect of p-tert.-butyl-alpha-methyldihydrocinnamaldehyde, although none of the compounds a), b) and d) itself exhibits an odor comprising a fresh laundry or a powdery aspect.

The olfactory properties of compounds a) and b) are as described above.

The olfactory properties of citronellyloxyacetaldehyde (Mugenal, hereinbelow referred to as compound d)) are described by the expert as comprising the following aspects:
 white blossom (especially lily of the valley)
 metallic (hot iron).

Combining the compounds a), b) and d) results in a preferred fragrance mixture having olfactory properties comprising the following aspects:
 white blossom (mainly lilac, but also lily of the valley)
 floral
 fresh (resembling fresh laundry)
 soft
 warm
 dry
 powdery
 crème-like
 cosmetically
 aldehyde-like
 hot iron Thus, a third preferred fragrance mixture of the invention which comprises or consists of the compounds a), b) and d) is capable of imitating and recreating a wide range of the specific olfactory aspects of p-tert.-butyl-alpha-methyldihydrocinnamaldehyde, including the white lilac blossom aspect, and the powdery aspect which hitherto has been considered as inimitable, and the fresh laundry aspect.

In an above-described third preferred fragrance mixture of the invention the amounts of compounds a), b) and d) and/or their ratio are preferably adjusted in order to optimize the olfactory properties of the mixture. More preferably the amounts of compounds a), b) and d) and/or their ratio are adjusted so that the mixture provides an odor comprising a white lilac blossom aspect resembling the white lilac blossom aspect of p-tert.-butyl-alpha-methyldihydrocinnamaldehyde, a fresh laundry aspect resembling the fresh laundry aspect of p-tert.-butyl-alpha-methyldihydrocinnamaldehyde and a powdery aspect resembling the powdery aspect of p-tert.-butyl-alpha-methyldihydrocinnamaldehyde.

Preferably an above-described third preferred fragrance mixture of the present invention comprises the compounds a) and b) in a weight ratio in the range of from 2.5:1 to 100:1, preferably in the range of from 3.5:1 to 20:1.

More preferably an above-described third preferred fragrance mixture of the invention comprises or consists of
 70-98.9% by weight, preferably 75-95% by weight of compound a),
 1-25% by weight, preferably 4.8-21% by weight of compound b),
 0.1-5% by weight, preferably 0.2-4% by weight of compound d),
based on the total amount of compounds a), b), c), d), e) and f) in the mixture.

Further preferably, an above-described third preferred fragrance mixture is a fragrance mixture according to an alternative (iii) of the invention. A fragrance mixture according to alternative (iii) of the invention comprises or consists of
 70-98.9% by weight, preferably 75-95% by weight of compound a),
 1-25% by weight, preferably 4.8-21% by weight of compound b),
 0% by weight of compound c),
 0.1-5% by weight, preferably 0.2-4% by weight of compound d),
 0% by weight of compound e),
 0% by weight of compound f),
based on the total amount of compounds a), b), c), d), e) and f) in the mixture.

An amount of compound d) of less than 0.1% and, accordingly a total amount of compounds a) and b) of more than 99.9% might result in a predominance of olfactory aspects of any combination of compounds a) and b) or—depending on their amounts and their ratio—any of the individual compounds a) and b) so that the desired olfactory aspects of a combination of compounds a), b) and d), especially according to alternative (iii), which imitate and recreate the corresponding olfactory aspects of p-tert.-butyl-alpha-methyldihydrocinnamaldehyde may be suppressed at least to some extent.

On the other hand an amount of compound d) of more than 5% and, accordingly a total amount of compounds a) and b) of less than 95% might result in a predominance of olfactory aspects of compound d), e.g. the hot iron aspect so that the desired olfactory aspects of a combination of compounds a), b) and d), especially according to alternative (iii), which imitate and recreate the corresponding olfactory aspects of p-tert.-butyl-alpha-methyldihydrocinnamaldehyde may be suppressed at least to some extent.

An above-described third preferred fragrance mixture of the invention, especially according to alternative (iii), has a substantivity and diffusivity of the fragrance which is even stronger than that of an above-described first and second preferred fragrance mixture of the invention, especially upon storage of laundry to which the mixture was applied. More preferably, an above-described third preferred fragrance mixture of the invention, especially according to alternative (iii) is characterized by a diffusivity value in the range of from 5.4 to 6.0 (in particular the value is preferably 5.7) and/or a substantivity value in the range of from 3.6 to 4.0 (in particular the value is preferably 3.8).

A fourth preferred fragrance mixture of the invention comprises or consists of
a) 2,2-dimethyl-3-(3-methylphenyl)-propanol (Majantol)
b) 4,4a,5,9b-tetrahydro-2,4-dimethylindenol[1,2-d]-m-dioxin (Magnolan)
c) 2-isobutyl-4-methyltetrahydro-2H-pyran-4-ol (Florosa)
d) citronellyloxyacetaldehyde (Mugenal)
and preferably none of the compounds e) and f).

Surprisingly it was found that a combination of compounds a), b), c) and d) is able to imitate and recreate not only the white lilac blossom aspect but also some other specific olfactory aspects of p-tert.-butyl-alpha-methyldihydrocinnamaldehyde which are not present in the odor of any of the individual compounds a), b), c) and d). Especially surprisingly a combination of compounds a), b), c) and d) is capable of imitating and recreating the well-balanced, harmonic powdery aspect of p-tert.-butyl-alpha-methyldihydrocinnamaldehyde, although none of the compounds a), b), c) and d) itself exhibits an odor comprising a powdery aspect.

The olfactory properties of compounds a), b), c) and d) are as described above.

Combining the compounds a), b), c) and d) results in a preferred fragrance mixture having olfactory properties comprising the following aspects:
white blossom (mainly lilac, but also lily of the valley)
floral (with an increased diffusivity of the floral aspects)
fresh (resemblance of fresh laundry similar to p-tert.-butyl-alpha-methyldihydrocinnamaldehyde)
soft
warm
dry
powdery (in a well-balanced harmonic manner resembling that of p-tert.-butyl-alpha-methyldihydrocinnamaldehyde)
crème-like
cosmetically
aldehyde-like
hot iron Thus, a fourth preferred fragrance mixture of the invention which comprises or consists of the compounds a), b), c) and d) is capable of imitating and recreating a wide range of the specific olfactory aspects of p-tert.-butyl-alpha-methyldihydro-cinnamaldehyde, including the white lilac blossom aspect, the well-balanced harmonic powdery aspect which hitherto has been considered as inimitable, and the fresh laundry aspect.

In an above-described fourth preferred fragrance mixture of the invention the amounts of compounds a), b), c) and d) and/or their ratio are preferably adjusted in order to optimize the olfactory properties of the mixture. More preferably the amounts of compounds a), b), c) and d) and/or their ratio are adjusted so that the mixture provides an odor comprising a white lilac blossom aspect resembling the white lilac blossom aspect of p-tert.-butyl-alpha-methyldihydrocinnamaldehyde, a fresh laundry aspect resembling the fresh laundry aspect of p-tert.-butyl-alpha-methyldihydrocinnamaldehyde and a well-balanced harmonic powdery aspect resembling the well balanced harmonic powdery aspect of p-tert.-butyl-alpha-methyldihydrocinnamaldehyde.

Preferably an above-described fourth preferred fragrance mixture of the invention comprises the compounds a) and b) in a weight ratio in the range of from 2.5:1 to 100:1, preferably in the range of from 4:1 to 17:1.

More preferably an above-described fourth preferred fragrance mixture comprises or consists of
  55-97.9% by weight, preferably 65-85% by weight of compound a),
  1-20% by weight, preferably 5-16% by weight of compound b),
  1-20% by weight, preferably 5-16% by weight of compound c),
  0.1-5% by weight, preferably 0.2-3% by weight of compound d),
based on the total amount of compounds a), b), c), d), e) and f) in the mixture.

Further preferably, an above-described fourth preferred fragrance mixture is a fragrance mixture according to an alternative (iv) of the invention. A fragrance mixture according to alternative (iv) of the invention comprises or consists of
  55-97.9% by weight, preferably 65-85% by weight of compound a),
  1-20% by weight, preferably 5-16% by weight of compound b),
  1-20% by weight, preferably 5-16% by weight of compound c),
  0.1-5% by weight, preferably 0.2-3% by weight of compound d),
  0% by weight of compound e),
  0% by weight of compound f),
based on the total amount of compounds a), b), c), d), e) and f) in the mixture.

An amount of compound d) of less than 0.1% might result in a predominance of olfactory aspects of a combination of any of compounds a), b) and c) or—depending on their amounts and their ratio—any of the individual compounds a), b) and c) so that the desired olfactory aspects of a combination of compounds a), b), c) and d), especially according to alternative (iv) of the invention, which imitate and recreate the corresponding olfactory aspects of p-tert.-butyl-alpha-methyldihydrocinnamaldehyde may be suppressed at least to some extent.

Correspondingly, an amount of compound c) of less than 1% might result in a predominance of olfactory aspects of a combination of any of compounds a), b) and d) or—depending on their amounts and their ratio—any of the individual compounds a), b) and d) so that the desired olfactory aspects of a combination of compounds a), b), c) and d), especially according to alternative (iv) of the invention, which imitate and recreate the corresponding olfactory aspects of p-tert.-butyl-alpha-methyldihydrocinnamaldehyde may be suppressed at least to some extent.

On the other hand an amount of compound d) of more than 5% might result in a predominance of olfactory aspects of compound d), e.g. the hot iron aspect, so that the desired olfactory aspects of a combination of compounds a), b), c) and d), especially according to alternative (iv) of the invention, which imitate and recreate the corresponding olfactory aspects of p-tert.-butyl-alpha-methyldihydrocinnamaldehyde may be suppressed at least to some extent.

Correspondingly, an amount of compound c) of more than 20% might result in a predominance of olfactory aspects of compound c), e.g. the white rose blossom aspect so that the desired olfactory aspects of a combination of compounds a), b), c) and d), especially according to alternative (iv) of the invention, which imitate and recreate the corresponding olfactory aspects of p-tert.-butyl-alpha-methyldihydrocinnamaldehyde may be suppressed at least to some extent.

An above described fourth preferred fragrance mixture of the invention, especially according to alternative (iv), has a substantivity and diffusivity of the fragrance which is even stronger than that of any above-described other preferred fragrance mixture of the invention, especially upon storage of laundry to which the mixture was applied. More preferably, an above-described fourth preferred fragrance mixture of the invention, especially according to alternative (iv) is characterized by a diffusivity value in the range of from 6.1 to 6.7 (in particular the value is preferably 6.4) and/or a substantivity value in the range of from 3.8 to 4.2 (in particular the value is preferably 4).

A fifth preferred fragrance mixture of the invention comprises or consists of
a) 2,2-dimethyl-3-(3-methylphenyl)-propanol (Majantol)
b) 4,4a,5,9b-tetrahydro-2,4-dimethylindenol[1,2-d]-m-dioxin (Magnolan)
c) 2-isobutyl-4-methyltetrahydro-2H-pyran-4-ol (Florosa)
d) citronellyloxyacetaldehyde (Mugenal)
e) 4-n-decylpyridine (Symmarine)
and preferably not the compound f).

Surprisingly it was found that a combination of compounds a), b), c), d) and e) is able to imitate and recreate not only the white lilac blossom aspect but also some other specific olfactory aspects of p-tert.-butyl-alpha-methyldihydrocinnamaldehyde which are not present in the odor of any of the individual compounds a), b), c) d) and e). Especially surprisingly a combination of compounds a), b), c), d) and e) is capable of imitating and recreating the well-balanced, harmonic powdery aspect of p-tert.-butyl-alpha-methyldihydrocinnamaldehyde in a manner which is even stronger than that of the above-described third and fourth preferred fragrance mixture of the invention, although none of the compounds a), b), c), d) and e) itself exhibits an odor comprising a powdery aspect. On the other hand, those individual olfactory aspects of the above compounds which are not in accordance with the olfactory properties of p-tert.-butyl-alpha-methyldihydrocinnamaldehyde, are not present in the odor of the combination of compounds a), b), c), d) and e).

The olfactory properties of compounds a), b), c) and d) are as described above.

The olfactory properties of 4-n-decylpyridine (Symmarine, hereinbelow referred to as compound e)) are described by the expert as comprising the following aspects:
maritime
cool
watery
algae-like.

Combining the compounds a), b), c), d) and e) results in a preferred fragrance mixture having olfactory properties comprising the following aspects:
white blossom (mainly lilac, but also lily of the valley)
floral (with an increased diffusivity of the floral aspects)
fresh (with an increased resemblance of fresh laundry similar to p-tert.-butyl-alpha-methyldihydrocinnamaldehyde)
soft
warm
dry
powdery (wherein this aspect has a well-balanced harmonic manner resembling that of p-tert.-butyl-alpha-methyldihydrocinnamaldehyde and is even stronger than in the above-described fourth preferred fragrance mixture)
crème-like
cosmetically
aldehyde-like
metallic (hot iron).

Thus, a fifth preferred fragrance mixture of the invention which comprises or consists of the compounds a), b), c), d) and e) is capable of imitating and recreating a wide range of the specific olfactory aspects of p-tert.-butyl-alpha-methyl-dihydro-cinnamaldehyde, including the white lilac blossom aspect, the well-balanced harmonic powdery aspect which hitherto has been considered as inimitable, and the fresh laundry aspect.

In an above-described fifth preferred fragrance mixture of the invention the amounts of compounds a), b), c), d) and e) and/or their ratio are preferably adjusted in order to optimize the olfactory properties of the mixture. More preferably the amounts of compounds a), b), c), d) and e) and/or their ratio are adjusted so that the mixture provides an odor comprising a white lilac blossom aspect resembling the white lilac blossom aspect of p-tert.-butyl-alpha-methyldihydrocinnamaldehyde, a fresh laundry aspect resembling the fresh laundry aspect of p-tert.-butyl-alpha-methyldihydro-cinnamaldehyde, and a well-balanced harmonic powdery aspect resembling the well balanced harmonic powdery aspect of p-tert.-butyl-alpha-methyldihydrocinnamaldehyde in an improved manner compared to the above-described fourth preferred fragrance mixture of the invention.

Preferably an above-described fifth preferred fragrance mixture of the invention comprises the compounds a) and b) in a weight ratio in the range of from 2.5:1 to 100:1, preferably in the range of from 4:1 to 17:1.

More preferably an above-described fifth preferred fragrance mixture comprises or consists of
54.98-97.8999% by weight, preferably 65-85% by weight of compound a),
1-20% by weight, preferably 5-16% by weight of compound b),
1-20% by weight, preferably 5-16% by weight of compound c),
0.1-5% by weight, preferably 0.2-2.98% by weight of compound d),
0.0001-0.02% by weight preferably 0.001-0.02% by weight of compound e),
based on the total amount of compounds a), b), c), d), e) and f) in the mixture.

Further preferably, an above-described fifth preferred fragrance mixture is a fragrance mixture according to an alternative (v) of the invention. A fragrance mixture according to alternative (v) of the invention comprises or consists of
54.98-97.8999% by weight, preferably 65-85% by weight of compound a),
1-20% by weight, preferably 5-16% by weight of compound b),
1-20% by weight, preferably 5-16% by weight of compound c),
0.1-5% by weight, preferably 0.2-2.98% by weight of compound d),
0.0001-0.02% by weight preferably 0.001-0.02% by weight of compound e),
0% by weight of compound f),
based on the total amount of compounds a), b), c), d), e) and f) in the mixture.

An amount of compound e) of less than 0.0001% might result in a predominance of olfactory aspects of a combination of any of compounds a), b), c) and d) or—depending on their amounts and their ratio—any of the individual compounds a), b), c) and d) so that the desired olfactory aspects of a combination of compounds a), b), c), d) and e), especially according to alternative (v) of the invention, which imitate and recreate the corresponding olfactory aspects of p-tert.-butyl-alpha-methyldihydrocinnamaldehyde may be suppressed at least to some extent.

On the other hand an amount of compound e) of more than 0.02% might result in a predominance of olfactory aspects of compound e), e.g. the maritime, cool, watery or algae-like aspects so that the desired olfactory aspects of a combination of compounds a), b), c), d) and e), especially according to alternative (v) of the invention, which imitate and recreate the corresponding olfactory aspects of p-tert.-butyl-alpha-methyldihydrocinnamaldehyde may be suppressed at least to some extent.

An above-described fifth preferred fragrance mixture of the invention, especially according to alternative (v), has a substantivity and diffusivity of the fragrance which is even stronger than that of any above-described other preferred fragrance mixture, especially upon storage of laundry to which the mixture was applied. More preferably, an above-described fifth preferred fragrance mixture of the invention, especially according to alternative (v) is characterized by a diffusivity value in the range of from 6.1 to 6.7 (in particular the value is preferably 6.4) and/or a substantivity value in the range of from 4.1 to 4.5 (in particular the value is preferably 4.3).

A sixth preferred fragrance mixture of the invention comprises or consists of
a) 2,2-dimethyl-3-(3-methylphenyl)-propanol (Majantol)
b) 4,4a,5,9b-tetrahydro-2,4-dimethylindenol[1,2-d]-m-dioxin (Magnolan)
c) 2-isobutyl-4-methyltetrahydro-2H-pyran-4-ol (Florosa)
d) citronellyloxyacetaldehyde (Mugenal)
e) 4-n-decylpyridine (Symmarine)
f) 4-(4-methyl-3-penten-1-yl)-3-cyclohexene carboxaldehyde (Vertomugal).

Surprisingly it was found that a combination of compounds a), b), c), d), e) and f) is able to imitate and recreate not only the white lilac blossom aspect but also some other specific olfactory aspects of p-tert.-butyl-alpha-methyldihydrocinnamaldehyde which are not present in the odor of any of the individual compounds a), b), c), d), e) and f). Especially surprisingly a combination of compounds a), b), c), d), e) and f) is capable of imitating and recreating the well-balanced, harmonic powdery aspect of p-tert.-butyl-alpha-methyldihydrocinnamaldehyde in a manner which is even stronger than that of the above-described third, fourth and fifth preferred fragrance mixture of the invention although none of the compounds a), b), c), d), e) and f) itself exhibits an odor comprising a powdery aspect. On the other hand, those individual olfactory aspects of the above compounds which are not in accordance with the olfactory properties of p-tert.-butyl-alpha-methyldihydrocinnamaldehyde, are not present in the odor of the combination of compounds a), b), c), d), e) and f).

The olfactory properties of compounds a), b), c), d) and e) are as described above.

The olfactory properties of 4-(4-methyl-3-penten-1-yl)-3-cyclohexene carboxaldehyde (Vertomugal, hereinbelow referred to as compound f)) are described by the expert as comprising the following aspects:
fresh laundry
aldehyde-like
red blossom (red lilac, red magnolia)
bread-like
fatty ozone-like
rancid Combining the compounds a), b), c), d), e) and f) results in a preferred fragrance mixture having olfactory properties comprising the following aspects:
white blossom (mainly lilac, but also lily of the valley)
floral (with an increased diffusivity of the floral aspects)
fresh (with an increased resemblance of fresh laundry similar to p-tert.-butyl-alpha-methyldihydrocinnamaldehyde)
soft
warm
dry
powdery (further increased)
crème-like
cosmetically
aldehyde-like
metallic (hot iron)

Thus, a sixth preferred fragrance mixture of the invention which comprises or consists of the compounds a), b), c), d), e) and f) is capable of imitating and recreating a wide range of the specific olfactory aspects of p-tert.-butyl-alpha-methyldihydrocinnamaldehyde, including the white lilac blossom aspect, and the well-balanced harmonic powdery aspect which hitherto has been considered as inimitable.

In an above-described sixth preferred fragrance mixture of the invention the amounts of compounds a), b), c), d), e) and f) and/or their ratio are preferably adjusted in order to optimize the olfactory properties of the mixture. More preferably the amounts of compounds a), b), c), d), e) and f) and/or their ratio of are adjusted so that the mixture provides an odor comprising a white lilac blossom aspect resembling the white lilac blossom aspect of p-tert.-butyl-alpha-methyldihydrocinnamaldehyde and a powdery aspect resembling the powdery aspect of p-tert.-butyl-alpha-methyldihydrocinnamaldehyde Preferably an above-described sixth preferred fragrance mixture of the invention comprises the compounds a) and b) in a weight ratio in the range of from 1.5:1 to 100:1, preferably in the range of from 2.5:1 to 17:1.

Further preferably, an above-described sixth preferred fragrance mixture is a fragrance mixture according to an alternative (vi) of the invention. A fragrance mixture according to alternative (vi) of the invention comprises or consists of
  34.98-96.8999% by weight, preferably 40-70% by weight of compound a),
  1-20% by weight, preferably 4-16% by weight of compound b),
  1-20% by weight, preferably 4-16% by weight of compound c),
  0.1-5% by weight, preferably 0.2-2.98% by weight of compound d),
  0.0001-0.02% by weight, preferably 0.001-0.02% by weight of compound e),
  5-30% by weight, preferably 10-29% by weight of compound f),
based on the total amount of compounds a), b), c), d), e) and f) in the mixture.

An amount of compound f) of less than 5% might result in a predominance of olfactory aspects of a combination of any of compounds a), b), c), d) and e) or—depending on their amounts and their ratio—any of the individual compounds a), b), c), d) and e) so that the desired olfactory aspects of a combination of compounds a), b), c), d), e) and f), especially according to alternative (vi) of the invention, which imitate and recreate the corresponding properties of p-tert.-butyl-alpha-methyldihydrocinnamaldehyde may be suppressed at least to some extent.

On the other hand an amount of compound f) of more than 30% might result in a predominance of individual olfactory aspects of compound f), e.g. the red blossom (red lilac, red magnolia), bread-like, fatty ozone-like, rancid aspects so that the desired olfactory aspects of a combination of compounds a), b), c), d), e) and f), especially according to alternative (vi) of the invention, which imitate and recreate the corresponding olfactory aspects of p-tert.-butyl-alpha-methyldihydrocinnamaldehyde may be suppressed at least to some extent.

Preferably, an above-described sixth preferred fragrance mixture of the invention, especially according to alternative (vi), has a substantivity and diffusivity of the fragrance which still stronger than that of any above-described other preferred fragrance mixture of the invention, especially upon storage of laundry to which the mixture was applied. More preferably, an above-described sixth preferred fragrance mixture of the invention, especially according to alternative (vi) is characterized by a diffusivity value in the range of from 6.2 to 6.8 (in particular the value is preferably 6.5) and/or a substantivity value in the range of from 4.4 to 4.8 (in particular the value is preferably 4.6). The olfactory aspects of the individual compounds and of the above-described preferred fragrance mixtures according to alternatives (i), (ii), (iii), (iv), (v) and (vi) of the invention are compiled in table 2.

TABLE 1

| | compounds comprised in mixtures of the invention (description of the pure compounds) | | | | | | (preferred) mixtures according to the invention | | | | |
|---|---|---|---|---|---|---|---|---|---|---|---|
| | Majantol (a) | Magnolan (b) | Florosa (c) | Mugenal (d) | Sym marine (e) | Vertomugal (f) | a: 70-99 wt % b: 1-30 wt % | a: 55-98 wt % b: 1-25 wt % c: 1-20 wt % | a: 70-98.9 wt % b: 1-20 wt % d: 0.1-5 wt % | a: 55-97.9 wt % b: 1-20 wt % c: 1-20 wt % d: 0.1-5 wt % | a: 54.99-97.8999 wt % b: 1-20 wt % c: 1-20 wt % d: 0.1-5 wt % e: 0.0001-0.01 wt % | a: 34.99-96.8999 wt % b: 1-20 wt % c: 1-20 wt % d: 0.1-5 wt % e: 0.0001-0.01 wt % f: 1-20 wt % |
| Lilial | white blossom (lilac, lily of the valley) floral | white blossom (lily of the valley) floral | white blossom (white magnolia) floral (red blossom, peony, geranium) | white blossom (white rose) | white blossom (lily of the valley) | | red blossom (red lilac, red magnolia) | white blossom (mainly lilac, also lily of the valley) Floral | white blossom (mainly lilac, also lily of the valley) floral | white blossom (mainly lilac, also lily of the valley) floral | white blossom (mainly lilac, also lily of the valley) floral (with an increased diffusivity) | white blossom (mainly lilac, also lily of the valley) floral (with an increased diffusivity) |
| powdery | | | | | | | | powdery | powdery | powdery (well-balanced harmonic manner similar to Lilial) | powdery (well-balanced harmonic manner close to Lilial) | powdery (further increased) |
| crème-like cosmetically aldehyde-like | | | | | | aldehyde-like | | crème-like cosmetically | crème-like cosmetically aldehyde-like | crème-like cosmetically aldehyde-like | crème-like cosmetically aldehyde-like | crème-like cosmetically aldehyde-like |
| warm dry soft | soft | | | | | | Warm Dry Soft | warm dry soft | warm dry soft | warm dry soft | warm dry soft | warm dry soft |
| fresh (fresh laundry) | fresh | | fresh | | | fresh laundry | Fresh | fresh | fresh (fresh laundry) | fresh (fresh laundry similar to Lilial) | fresh (fresh laundry close to Lilial) | fresh (fresh laundry close to Lilial) |
| hot-iron-like | | indol-like | | hot iron | maritime cool watery algae-like | bread-like fatty ozone-like rancid | | | hot iron | hot iron | hot iron | hot iron |

The invention also relates to a fragrance composition comprising an organoleptically effective amount of a fragrance mixture of the invention, especially one selected from the above-described preferred fragrance mixtures. A fragrance composition of the invention may contain further ingredients, e.g. conventional fragrance substances and/or other auxiliary or functional substances.

Conventional fragrance substances with which a fragrance mixture of the invention can advantageously be combined to form a fragrance composition of the present invention, especially for use in a perfumed product, are disclosed e.g. in Steffen Arctander, Perfume and Flavor Chemicals, private publishing house, Montclair, N.J., 1969; H. Surburg, J. Panten, Common Fragrance and Flavor Materials, 5th Edition, Wiley-VCH, Weinheim 2006.

Beside p-tert.-butyl-alpha-methyldihydrocinnamaldehyde there may be mentioned in detail:

extracts from natural raw materials, such as essential oils, concretes, absolutes, resins, resinoids, balsams, tinctures, such as e.g. amber tincture; amyris oil; angelica seed oil; angelica root oil; aniseed oil; valerian oil; basil oil; tree moss absolute; bay oil; artemisia oil; benzoin resin; bergamot oil; beeswax absolute; birch tar oil; bitter almond oil; bean leaf oil; buchu leaf oil; cabreuva oil; cade oil; calamus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiva balsam; copaiva balsam oil; coriander oil; costus root oil; cumin oil; cypress oil; davana oil; dill weed oil; dill seed oil; eau de brouts absolute; oak moss absolute; elemi oil; tarragon oil; *Eucalyptus citriodora* oil; *eucalyptus* oil; fennel oil; spruce needle oil; galbanum oil; galbanum resin; geranium oil; grapefruit oil; guaiac wood oil; gurjunene balsam; gurjunene balsam oil; helichrysum absolute; helichrysum oil; ginger oil; iris root absolute; iris root oil; jasmine absolute; calamus oil; camomile oil blue; camomile oil Roman; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon grass oil; lovage oil; lime oil distilled; lime oil pressed; linaloa oil; *Litsea cubeba* oil; bay leaf oil; mace oil; marjoram oil; mandarin oil; massoi bark oil; mimosa absolute; musk seed oil; musk tincture; muscatel sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; oregano oil; palmarosa oil; patchouli oil; perilla oil; Peru balsam oil; parsley leaf oil; parsley seed oil; petitgrain oil; peppermint oil; pepper oil; pimento oil; pine oil; poley oil; rose absolute; rose wood oil; rose oil; rosemary oil; sage oil Dalmatian; sage oil Spanish; sandalwood oil; celery seed oil; spike lavender oil; star aniseed oil; styrax oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; hyssop oil; civet absolute; cinnamon leaf oil; cinnamon bark oil; and fractions thereof or constituents isolated therefrom;

individual fragrance compounds from the group consisting of the hydrocarbons, such as e.g. 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

the aliphatic alcohols, such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene;

the aliphatic ketones and oximes thereof, such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; the aliphatic sulfur-containing compounds, such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles, such as e.g. 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

the aliphatic carboxylic acids and esters thereof, such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynate; methyl 2-nonynate; allyl 2-isoamyloxyacetate; methyl 3,7-dimethyl-2,6-octadienoate;

the acyclic terpene alcohols, such as e.g. citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

the acyclic terpene aldehydes and ketones, such as e.g. geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

the cyclic terpene alcohols, such as e.g. menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

the cyclic terpene aldehydes and ketones, such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alphairone; alpha-damascone; beta-damascone; beta-damascenone; deltadamascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedar wood oil (methyl cedryl ketone);

the cyclic alcohols, such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol;

the cycloaliphatic alcohols, such as e.g. alpha,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers, such as e.g. cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose-oxide; 2-(2,4-dimethyl-3-cyclohexen-1-yl)-5-methyl-5-(1-methylpropyl)-1,3-dioxane;

the cyclic ketones, such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 7-cyclohexadecen-1-one; 8-cyclohexadecen-1-one; 6,7-dihydro-1,1,2,3,3-pentamethyl-4(5H)-indanone; 9-cycloheptadecen-1-one; cyclopentadecanone; cyclohexadecanone;

the cycloaliphatic aldehydes, such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones, such as e.g. 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl(2,4-dimethyl-3-cyclohexen-1-yl) ketone;

the esters of cyclic alcohols, such as e.g. 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- and -6-indenyl acetate; 4,7-methano-3a,4,5,6,7,7a-hexahydro-5- and -6-indenyl propionate; 4,7-methano-3a,4,5,6,7,7a-hexahydro-5- and -6-indenyl isobutyrate; 4,7-methanooctahydro-5- and 6-indenyl acetate;

the esters of cycloaliphatic carboxylic acids, such as e.g. allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the aromatic hydrocarbons, such as e.g. styrene and diphenylmethane;

the araliphatic alcohols, such as e.g. benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids, such as e.g.: benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; the araliphatic ethers, such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydro-2,4-dimethylindeno[1,2-d]-m-dioxin;

the aromatic and araliphatic aldehydes, such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones, such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl-methyl ketone; 1-[2,3-dihydro-1,1,2,6-tetramethyl-3-(1-methylethyl)-1H-5-indenyl]-ethanone; 5',6',7',8'-tetrahydro-3',5',5,6',8',8'-hexamethyl-2-acetonaphthone;

the aromatic and araliphatic carboxylic acids and esters thereof, such as e.g. benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds, such as e.g. 2,4,6-trinitro-1,3-dimethyl-5-tert-butylbenzene; 3,5-dinitro-2,6-dimethyl-4-tert-butylacetophenone; cinnamic acid nitrile; 5-phenyl-3-methyl-2-pentenoic acid nitrile; 5-phenyl-3-methylpentanoic acid nitrile; methyl anthranilate; methyl N-methylanthranilate; Schiff's bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

the phenols, phenyl ethers and phenyl esters, such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds, such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones, such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

A fragrance composition of the invention can be employed in liquid form, undiluted or diluted with a solvent. Suitable solvents for this are e.g. ethanol, isopropanol, diethylene glycol monoethyl ether, glycerol, propylene glycol, 1,2-butylene glycol, dipropylene glycol, diethyl phthalate, triethyl citrate, isopropyl myristate. In the context of the present text, the solvents mentioned are not interpreted as fragrance compounds.

For some uses, it is advantageous to employ a fragrance composition comprising a fragrance mixture of the invention which is adsorbed on a carrier substance, which ensures both a fine distribution of the fragrance mixture in the product and a controlled release during use. Such carriers can be porous inorganic materials, such as light sulfate, silica gels, zeolites, gypsums, clays, clay granules, gas concrete etc., or organic materials, such as woods; cellulose-based substances, sugars or plastics, such as PVC, polyvinyl acetates or polyurethanes.

For other uses, it is advantageous to employ a fragrance composition which comprises a fragrance mixture of the invention in microencapsulated or spray-dried form or in the form of an inclusion complex or an extrusion product and to add them in this form to a product to be perfumed.

The properties of fragrance compositions of the invention modified in this manner are in some cases optimized further in respect of a more controlled release of fragrance by so-called "coating" with suitable materials, for which purpose wax-like plastics, such as e.g. polyvinyl alcohol, are preferably used.

The microencapsulation of fragrance compositions can be carried out, for example, by the co-called coacervation process with the aid of capsule materials e.g. of polyurethane-like substances or soft gelatine. The spray-dried fragrance compositions can be prepared, for example, by spray drying of an emulsion or dispersion containing the fragrance composition, it being possible to use modified starches, proteins, dextrin and plant gums as carrier substances. Inclusion complexes can be prepared e.g. by introducing dispersions of the fragrance composition and cyclodextrins or urea derivatives into a suitable solvent, e.g. water. Extrusion products can be achieved by melting the fragrance compositions with a suitable wax-like substance and by extrusion with subsequent solidification, optionally in a suitable solvent, e.g. isopropanol.

Further ingredients with which a fragrance mixture of the invention can be combined are, for example:

preservatives, abrasives, antiacne agents, agents against ageing of the skin, antibacterial agents, anticellulitis agents, antidandruff agents, antiinflammatory agents, irritation-preventing agents, irritation-inhibiting agents, antimicrobial agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, fungicides, gelling agents, gel-forming agents, hair care agents, hair setting agents, hair straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin soothing agents, skin cleansing agents, skin care agents, skin healing agents, skin lightening agents, skin protecting agents, skin softening agents, cooling agents, skin cooling agents, warming agents, skin warming agents, stabilizers, UV-absorbing agents, UV filters, detergents, laundry softeners, suspending agents, skin tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, fragrance compounds, polyols, surfactants, electrolytes, organic solvents or silicone derivatives.

The fragrance composition according to the invention may be a perfume oil.

Preferably, a fragrance composition of the invention exhibits at least certain olfactory properties which imitate and recreate the corresponding olfactory properties of p-tert.-butyl-alpha-methyldihydrocinnamaldehyde. These olfactory properties result from or are enhanced by the amount of the compounds a), b) and—if present—c), d), e) and/or f) of an above-described fragrance mixture which is present in the composition.

The extent to which a fragrance composition of the invention is able to imitate and recreate the olfactory properties of p-tert.-butyl-alpha-methyldihydrocinnamaldehyde depends on the composition and the amount of the fragrance mixture of the invention which is present in the fragrance composition.

Preferably a fragrance composition of the invention exhibits an odor comprising a white lilac blossom aspect, more preferably a white lilac blossom and a powdery aspect resulting from and/or enhanced by the amount of the compounds a), b) and—if present—c), d), e) and/or f) of an above-described fragrance mixture which is present in the fragrance composition.

Most preferably, a fragrance composition of the invention exhibits an odor comprising a white lilac blossom and a powdery aspect resulting from and/or enhanced by the amount of compounds a), b) and—whichever present—c), d), e) and/or f) of any of the above-described second, third, fourth, fifth and sixth preferred mixture of the invention, preferably a mixture selected from above-described alternatives (ii), (iii), (iv), (v) and (vi), which is present in the fragrance composition.

In a fragrance composition of the invention the amounts and/or the ratio of compounds a) and b) and—if present—c), d), e) and/or f) are preferably adjusted in order to optimize the olfactory properties of the fragrance composition. Preferably, in a fragrance composition of the invention the amounts and/or the ratio of the compounds a) and b) and—if present—c), d), e) and/or f) are adjusted so that the fragrance composition exhibits an odor comprising a white lilac blossom aspect resembling the white lilac blossom aspect of p-tert.butyl-alpha-methyldihydrocinnamaldehyde. More preferably in a fragrance composition of the invention the amount and the ratio of compounds a) and b) and—if present—c), d), e) and/or f) are adjusted so that the fragrance composition exhibits an odor comprising a white lilac blossom aspect and a powdery aspect. Most preferably the amounts and the ratio of compounds a), b) and—whichever present—c), d), e) and/or f) are adjusted so that the fragrance composition exhibits an odor comprising a white lilac blossom aspect and a powdery aspect resembling the powdery aspect of p-tert.-butyl-alpha-methyldihydrocinnamaldehyde.

A fragrance composition which exhibits an odor comprising a white lilac blossom aspect and a powdery aspect resembling the corresponding olfactory aspects of p-tert.-butyl-alpha-methyldihydrocinnamaldehyde can be obtained by combining a mixture selected from the above-described second, third, fourth, fifth and sixth preferred mixture of the invention, preferably a mixture selected from above-described alternatives (ii), (iii), (iv), (v) and (vi), with the other ingredients of the desired fragrance composition.

Usually a fragrance composition of the invention contains about 0.1 to 20% by weight of compounds a) and b) and—if present—c), d), e) and/or f), more preferably 0.5 to 14% by weight of compounds a) and b) and—if present—c), d), e) and/or f) and most preferably 1 to 10% by weight of compounds a) and b) and—if present—c), d), e) and/or f). As described above a fragrance mixture of the invention may be combined with p-tert.-butyl-alpha-methyldihydrocinnamaldehyde. It may be advantageous to combine p-tert.-butyl-alpha-methyldihydrocinnamaldehyde and a fragrance mixture of the invention in a fragrance composition because the olfactory effects obtainable with p-tert.-butyl-alpha-methyldihydrocinnamaldehyde when applied in the allowed range can be enhanced by replenishing a mixture of the invention, or the amount of p-tert.-butyl-alpha-methyldihydrocinnamaldehyde which is needed for a certain olfactory effect might be reduced by replacing it with a mixture of the invention.

More specifically, if a fragrance composition according to the invention further comprises p-tert.-butyl-alpha-methyldihydrocinnamaldehyde, the ratio in parts by weight of p-tert.butyl-alpha-methyldihydrocinnamaldehyde to the total amount of the compounds a), b) and—if present—c), d), e) and/or f) of the above-described fragrance mixture is in the range of from 10:1 to 1:20, preferably in the range of from 4:1 to 1:10.

Preferably a fragrance composition of the invention comprises only minor amounts of p-tert.-butyl-alpha-methyldihydrocinnamaldehyde. More preferably a fragrance composition of the invention comprises an amount of p-tert.-butyl-alpha-methyldihydrocinnamaldehyde below 3 wt.-% (but not more than the limit value determined by the IFRA for the respective product category, see table 1), more preferably less than an organoleptically and/or toxicologically effective amount of p-tert.-butyl-alpha-methyldihydrocinnamaldehyde, and especially preferable an amount of p-tert.-butyl-alpha-methyldihydro-cinnamaldehyde which is below the limit value which requires declaration of that substance on the product label. Most preferably a fragrance composition of the invention comprises no p-tert.-butyl-alpha-methyldihydro-cinnamaldehyde.

The fragrance mixtures as well as the fragrance compositions of the invention may be used to impart an odor to a product so that this product exhibits at least certain aspects of the odor of p-tert.-butyl-alpha-methyldihydrocinnamaldehyde, or to enhance the respective aspects in the odor of a product.

The invention also relates to a perfumed product comprising (i) a fragrance mixture of the invention as described above, especially one of the above-described preferred fragrance mixtures, or (ii) a fragrance composition of the invention as described above.

Preferably, the perfumed product of the invention is selected from the group consisting of perfume extracts, perfume waters, toilet waters, shaving lotions, cologne waters, pre-shave products, splash colognes and perfumed freshening wipes, as well as perfuming of acid, alkaline and neutral cleaning compositions, such as e.g. floor cleaners, window glass cleaners, dishwashing compositions, bath and sanitary cleaners, scouring milk, solid and liquid WC cleaners, powder and foam carpet cleaners, liquid detergents, pulverulent detergents, laundry pretreatment compositions, such as bleaching compositions, soaking compositions and stain removers, laundry softeners, washing soaps, washing tablets, disinfectants, surface disinfectants and air fresheners in liquid or gelatinous form or in a form applied to a solid carrier, aerosol sprays, waxes and polishes, such as furniture polishes, floor waxes, shoe creams as well as body care compositions, such as e.g. solid and liquid soaps, shower gels, shampoos, shaving soaps, shaving foams, bath oils, cosmetic emulsions of the oil-in-water, of the water-in-oil and of the water-in-oil-in-water type, such as e.g. skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products, such as e.g. hair sprays, hair gels, hair lotions, hair conditioners, permanent and semi-permanent hair colouring compositions, hair setting compositions, such as cold waving compositions and hair straightening compositions, hair waters, hair creams and lotions, deodorants and antiperspirants, such as e.g. underarm sprays, roll-ons, deodorant sticks, deodorant creams or products for decorative cosmetics. Particularly preferred perfumed products of the invention are detergents and hygiene or care products, in particular in the field of body care, cosmetics and household products.

Preferably, a perfumed product of the invention exhibits at least certain olfactory properties which imitate and recreate the corresponding olfactory properties of p-tert.-butylalpha-methyldihydrocinnamaldehyde. These olfactory properties result from or are enhanced by the amount of the compounds a), b) and—if present—c), d), e) and/or f) of an above described fragrance mixture which—either as such or as an ingredient of an above-described fragrance composition—is present in the perfumed product.

The extent to which the odor of a perfumed product of the invention imitates and recreates the olfactory properties of p-tert.-butyl-alpha-methyldihydrocinnamaldehyde depends on the composition and the amount of the fragrance mixture of the invention which—either as such or as an ingredient of an above-described fragrance composition—is present in the perfumed product.

Preferably a perfumed product of the invention exhibits an odor comprising a white lilac blossom aspect, more preferably a white lilac blossom and a powdery aspect resulting from and/or enhanced by the amount of the compounds a), b) and—if present—c), d), e) and/or f) of an above described fragrance mixture which—either as such or as an ingredient of an above-described fragrance composition—is present in the perfumed product.

Most preferably, a perfumed product of the invention exhibits an odor comprising a white lilac blossom and a powdery aspect resulting from and/or enhanced by the amount of compounds a), b) and—whichever present—c), d), e) and/or f) of a mixture selected from the above-described second, third, fourth, fifth and sixth preferred mixture of the invention, preferably a mixture selected from above-described alternatives (ii), (iii), (iv), (v) and (vi), which—either as such or as an ingredient of an above-described fragrance composition of the invention—is present in the perfumed product.

In a perfumed product of the invention the amounts and/or the ratio of compounds a) and b) and—if present—c), d), e) and/or f) are preferably adjusted in order to optimize the olfactory properties of the perfumed product. Preferably, in a perfumed product of the invention the amounts and/or the ratio of compounds a) and b) and—if present—c), d), e) and/or f) are adjusted so that the perfumed product exhibits an odor comprising a white lilac blossom aspect resembling the white lilac blossom aspect of p-tert.-butyl-alpha-methyldihydrocinnamaldehyde. More preferably in a perfumed product of the invention the amounts and the ratio of compounds a), b) and—if present—c), d), e) and/or f) are adjusted so that the perfumed product exhibits an odor comprising a white lilac blossom aspect and a powdery aspect. Most preferably the amounts and the ratio of compounds a), b) and—whichever present—c), d), e) and/or f) are adjusted so that the perfumed product exhibits an odor comprising a white lilac blossom aspect and a powdery aspect resembling the powdery aspect of p-tert.-butyl-alpha-methyldihydrocinnamaldehyde.

A perfumed product which exhibits an odor comprising a white lilac blossom aspect and a powdery aspect resembling the corresponding olfactory aspects of p-tert.-butyl-alpha-methyldihydrocinnamaldehyde can be obtained by including a mixture selected from the above-described second, third, fourth, fifth and sixth preferred fragrance mixture, preferably a mixture selected from above-described alternatives (ii), (iii), (iv), (v) and (vi), or a fragrance composition comprising a mixture selected from the above-described second, third, fourth, fifth and sixth preferred fragrance mixture, preferably a mixture selected from above-described alternatives (ii), (iii), (iv), (v) and (vi), into said product.

Usually a perfumed product of the invention contains about 0.05 to 5% by weight of compounds a), b) and—if present—c), d), e) and/or f), more preferably 0.1 to 2.5% by weight of compounds a), b) and—if present—c), d), e) and/or f) and most preferably 0.15 to 1% by weight of compounds a), b) and—if present—c), d), e) and/or f) of a mixture of the invention as described above which—either as such or as an ingredient of an above-described fragrance composition of the invention—is present in the perfumed product.

As explained above a fragrance mixture of the invention may be combined with p-tert.butyl-alpha-methyldihydrocinnamaldehyde. It may be advantageous to include a combination of p-tert.-butyl-alpha-methyldihydrocinnamaldehyde and a fragrance mixture of the invention in a perfumed product of the invention because the olfactory effects obtainable with p-tert.-butyl-alpha-methyldihydrocinnamaldehyde when applied in the allowed range can be enhanced by replenishing with a mixture of the invention, or the amount of p-tert.butyl-alpha-methyldihydrocinnamaldehyde which is needed for a certain olfactory effect might be reduced by replacing it with a mixture of the invention Preferably a perfumed product of the invention comprises only minor amounts of p-tert.butyl-alpha-methyldihydrocinnamaldehyde. More preferably a perfumed product of the invention comprises an amount of p-tert.-butyl-alpha-methyldihydrocinnamaldehyde below 3 wt.-% (but not more than the limit value determined by the IFRA for the respective product category, see table 1), more preferably less than an organoleptically and/or toxicologically effective amount of p-tert.-butyl-alpha-methyldihydro-cinnamaldehyde, and especially preferable an amount of p-tert.-butyl-alpha-methyldihydrocinnamaldehyde which is below the limit value which requires declaration of that substance on the product label. Preferably the perfumed product of the invention is a product of category 1, 2, 3, 4, 5, 6, 7, 8, 9 or 10 as defined in table 1 and comprises an amount of p-tert.-butyl-alpha-methyldihydrocinnamaldehyde in the range of from 0 to the limit value (as defined in table 1) for the respective product category. Most preferably a perfumed product of the invention comprises no p-tert.-butyl-alpha-methyldihydrocinnamaldehyde.

The invention also relates to a method of imparting an odor to a product or enhancing an odor of a product, comprising the step of adding to the product or incorporating into the product an organoleptically effective amount of (a) a fragrance mixture of the invention as described above or (b) a fragrance composition of the invention as described above.

Preferably, the product is selected from the group consisting of perfume extracts, perfume waters, toilet waters, shaving lotions, cologne waters, pre-shave products, splash colognes and perfumed freshening wipes, as well as perfuming of acid, alkaline and neutral cleaning compositions, such as e.g. floor cleaners, window glass cleaners, dishwashing compositions, bath and sanitary cleaners, scouring milk, solid and liquid WC cleaners, powder and foam carpet cleaners, liquid detergents, pulverulent detergents, laundry pretreatment compositions, such as bleaching compositions, soaking compositions and stain removers, laundry softeners, washing soaps, washing tablets, disinfectants, surface disinfectants and air fresheners in liquid or gelatinous form or in a form applied to a solid carrier, aerosol sprays, waxes and polishes, such as furniture polishes, floor waxes, shoe creams as well as body care compositions, such as e.g. solid and liquid soaps, shower gels, shampoos, shaving soaps, shaving foams, bath oils, cosmetic emulsions of the oil-in-water, of the water-in-oil and of the water-in-oil-in-water type, such as e.g. skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products, such as e.g. hair sprays, hair gels, hair lotions, hair conditioners, permanent and semi-permanent hair colouring compositions, hair setting compositions, such as cold waving compositions and hair straightening compositions, hair waters, hair creams and lotions, deodorants and antiperspirants, such as e.g. underarm sprays, roll-ons, deodorant sticks, deodorant creams or products for decorative cosmetics. Particularly preferred products are detergents and hygiene or care products, in particular in the field of body care, cosmetics and household products.

Preferably, by the method of the invention at least certain olfactory properties are imparted to a product which imitate and recreate the corresponding olfactory properties of p-tert.-butyl-alpha-methyldihydro-cinnamaldehyde, or such olfactory aspects of the odor of a product are enhanced by the method of the invention. These olfactory properties result from or are enhanced by the amount of the compounds a), b) and—if present—c), d), e) and/or f) of an above described fragrance mixture which according to the method of the invention is added to or incorporated in a product either directly or as an ingredient of a fragrance composition which is added to or incorporated in a product.

The extent to which the method of the invention is capable to impart to a product an odor which imitates and recreates the olfactory properties of p-tert.-butyl-alpha-methyldihydrocinnamaldehyde or to enhance such odor of a product depends on the composition and the amount of the fragrance mixture of the invention which according to the method of the invention is added to or incorporated in a product either directly or as an ingredient of a fragrance composition which is added to or incorporated in a product.

Preferably the odor which is imparted to a product by the method of the invention or the odor of a product which is enhanced by the method of the invention comprises a white lilac blossom aspect, more preferably a white lilac blossom and a powdery aspect resulting from and/or enhanced by the amount of the compounds a), and b), and—if present—c), d), e) and/or f) of an above-described fragrance mixture which according to the method of the invention is added to or incorporated in a product (either directly or as ingredient of a fragrance composition).

Most preferably, the odor which is imparted to a product by the method of the invention or the odor of a product which is enhanced by the method of the invention comprises a white lilac blossom and a powdery aspect resulting from and/or enhanced by the amount of the compounds a), b) and—whichever present—c), d), e) and/or f) of a mixture selected from the above-described second, third, fourth, fifth and sixth preferred fragrance mixture of the invention, preferably a mixture selected from above-described alternatives (ii), (iii), (iv), (v) and (vi), which is added to or incorporated in the product either directly or as ingredient of a fragrance composition which is added to or incorporated in a product.

In a fragrance mixture or a fragrance composition which is used in the method of the invention the amounts and/or the ratio of compounds a) and b) and—if present—c), d), e) and/or f) are preferably adjusted in order to optimize the olfactory properties of the product to be obtained. Preferably, in a fragrance mixture or a fragrance composition used in the method of the invention the amount and/or the ratio of compounds a) and b) and—if present—c), d), e) and/or f) are adjusted so that a product is obtained exhibiting an odor comprising a white lilac blossom aspect resembling the white lilac blossom aspect of p-tert.-butyl-alpha-methyldihydrocinnamaldehyde. More preferably in a fragrance mixture or fragrance composition used in the method of the invention the amounts and the ratio of the compounds a), b) and—if present—c), d), e) and/or f) are adjusted so that a product is obtained exhibiting an odor comprising a white lilac blossom aspect and a powdery aspect. Most preferably the amounts and the ratio of compounds a), b) and—whichever present—c), d), e) and/or f) are adjusted so that a product exhibiting an odor comprising a white lilac blossom aspect and a powdery aspect resembling the powdery aspect of p-tert.-butyl-alpha-methyldihydro-cinnamaldehyde is obtained.

A product which exhibits an odor comprising a white lilac blossom aspect and a powdery aspect resembling the corresponding olfactory aspects of p-tert.-butyl-alpha-methyldihydrocinnamaldehyde can be obtained by a method comprising the step of adding to a product or incorporating into a product a fragrance mixture selected from the above-described second, third, fourth, fifth and sixth preferred fragrance mixture, preferably a mixture selected from above-described alternatives (ii), (iii), (iv), (v) and (vi), or a fragrance composition comprising a mixture selected from the above-described second, third, fourth, fifth and sixth preferred fragrance mixture, preferably a mixture selected from above-described alternatives (ii), (iii), (iv), (v) and (vi).

In the method of the invention, usually a fragrance mixture of the invention or a fragrance composition of the invention is added to or incorporated in a product in such amount that the product after addition or incorporation of an above-described fragrance mixture or an above-described fragrance composition comprises about 0.05 to 5% by weight of a compounds a), b) and—if present—c), d), e) and/or f) is obtained, more preferably 0.1 to 2.5% by weight of a compounds a), b) and—if present—c), d), e) and/or f) and most preferably 0.15 to 1% by weight of a compounds a), b) and—if present—c), d), e) and/or f).

In the method of the invention a combination of a fragrance mixture of the invention and p-tert.-butyl-alpha-methyldihydrocinnamaldehyde may be added to or incorporated in a product. Adding a combination of p-tert.-butyl-alpha-methyldihydrocinnamaldehyde and a fragrance mixture of the invention to a product or incorporating a combination of p-tert.butyl-alpha-methyldihydrocinnamaldehyde and a fragrance mixture of the invention in a product may be advantageous because the olfactory effects obtainable with p-tert.-butyl-alpha-methyldihydrocinnamaldehyde when applied in the allowed range can be improved by replenishing with a mixture of the invention, or the amount of p-tert.-butyl-alpha-methyldihydrocinnamaldehyde which is needed for a certain olfactory effect might be reduced by replacing it with a mixture of the invention.

Preferably a product obtained by the method of the invention comprises only minor amounts of p-tert.-butyl-alpha-methyldihydrocinnamaldehyde. More preferably a p product obtained by the method of the invention comprises an amount of p-tert.-butyl-alpha-methyldihydro-cinnamaldehyde below 3 wt.-% (but not more than the limit value determined by the IFRA for the respective product category, see table 1), more preferably less than an organoleptically and/or toxicologically effective amount of p-tert.-butyl-alpha-methyldihydrocinnamaldehyde, and especially preferable an amount of p-tert.-butyl-alpha-methyldihydro-cinnamaldehyde which is below the limit value which requires declaration of that substance on the product label. Preferably the product obtained by the method of the invention is a product of category 1, 2, 3, 4, 5, 6, 7, 8, 9 or 10 as defined in table 1 and comprises an amount of p-tert.-butyl-alpha-methyldihydrocinnamaldehyde in the range of from 0 to the limit value (as defined in table 1) for the respective product category. Most preferably a product obtained by the method of the invention comprises no p-tert.-butyl-alpha-methyldihydrocinnamaldehyde.

The present invention also relates to the use of an above-described fragrance mixture especially one of the above-described preferred fragrance mixtures, for imitating and/or recreating olfactory aspects of p-tert.-butyl-alpha-methyldihydrocinnamaldehyde. Preferably an above-described fragrance mixture, especially one of the above-described preferred fragrance mixtures, is used for imitating and recreating the white lilac blossom aspect and optionally powdery aspects of p-tert.-butyl-alpha-methyldihydrocinnamaldehyde.

EXAMPLES

Example 1

Fragrance Mixture

A preferred fragrance mixture of the present invention has the following composition.

| component | wt.-% |
| --- | --- |
| a) 2,2-dimethyl-3-(3-methylphenyl)-propanol (Majantol) | 54.483 |
| b) 4,4a,5,9b-tetrahydro-2,4-dimethylindenol[1,2-d]-m-dioxin (Magnolan) | 7.609 |
| c) 2-isobutyl-4-methyltetrahydro-2H-pyran-4-ol (Florosa) | 9.436 |
| d) Citronellyloxyacetaldehyde (Mugenal) | 0.254 |
| e) 4-n-decylpyridine (Symmarine) | 0.012 |
| f) 4-(4-methyl-3-penten-1-yl)-3-cyclohexene carboxaldehyde (Vertomugal) | 28.206 |
| total | 100.000 |

Examples 2-8

Perfume Oil Compositions

| component | example 2 Parts by weight | example 3 Parts by weight | example 4 Parts by weight | example 5 Parts by weight | example 6 Parts by weight | example 7 Parts by weight | example 8 Parts by weight |
| --- | --- | --- | --- | --- | --- | --- | --- |
| (3AR-(3A.ALPHA,5A.ALPHA,9A.BETA,9B.BETA))-DODECAHYDRO-3A,6,6,9A-TETRAMETHYL-NAPHTO-(2,1-B)-FURANE | 2.500 | 2.500 | 2.500 | 2.500 | 2.500 | 2.500 | 2.500 |
| E/Z-7/8-CYCLOHEXADECENONE | 40.000 | 40.000 | 40.000 | 40.000 | 40.000 | 40.000 | 40.000 |
| BERGAMOT OIL RCO | 20.000 | 20.000 | 20.000 | 20.000 | 20.000 | 20.000 | 20.000 |
| 6,7-Dihydro-1,1,2,3,3-pentamethyl-4(5H)-indanon | 10.000 | 10.000 | 10.000 | 10.000 | 10.000 | 10.000 | 10.000 |
| CITRAL 10% in Triethyl citrate | 10.000 | 10.000 | 10.000 | 10.000 | 10.000 | 10.000 | 10.000 |
| CITRONELLOL | 5.000 | 5.000 | 5.000 | 5.000 | 5.000 | 5.000 | 5.000 |
| DECALACTONE GAMMA 10% in Triethyl citrate | 15.000 | 15.000 | 15.000 | 15.000 | 15.000 | 15.000 | 15.000 |
| DIMETHYL BENZYL CARBINYL ACETATE | 5.000 | 5.000 | 5.000 | 5.000 | 5.000 | 5.000 | 5.000 |
| DIPROPYLENE GLYCOL | 90.000 | 89.900 | 89.900 | 89.900 | 89.900 | 89.900 | 89.900 |
| ETHYLENE-UNDECANE-DICARBOXYLATE | 40.000 | 40.000 | 40.000 | 40.000 | 40.000 | 40.000 | 40.000 |
| EUGENOL 10% in Triethyl citrate | 5.000 | 5.000 | 5.000 | 5.000 | 5.000 | 5.000 | 5.000 |
| GERANIOL | 10.000 | 10.000 | 10.000 | 10.000 | 10.000 | 10.000 | 10.000 |
| METHYL-(2-PENTYL-3-OXO-1-CYCLO-PENTYL)-ACETATE | 200.000 | 200.000 | 200.000 | 200.000 | 200.000 | 200.000 | 200.000 |
| ALPHA METHYL-1,3-BENZODIOXOLE-5-PROPANAL | 25.000 | 25.000 | 25.000 | 25.000 | 25.000 | 25.000 | 25.000 |
| HEXENOL CIS-3 10% in Triethyl citrate | 15.000 | 15.000 | 15.000 | 15.000 | 15.000 | 15.000 | 15.000 |
| HEXENYL SALICYLATE CIS-3 | 30.000 | 30.000 | 30.000 | 30.000 | 30.000 | 30.000 | 30.000 |
| INDOLE 10% in Triethyl citrate | 5.000 | 5.000 | 5.000 | 5.000 | 5.000 | 5.000 | 5.000 |
| 2-ACETYL-1,2,3,4,5,6,7,8-OCTA-HYDRO-2,3,8,8-TETRAMETHYL-NAPHTALENE | 80.000 | 80.000 | 80.000 | 80.000 | 80.000 | 80.000 | 80.000 |
| ISOEUGENYL METHYL ETHER 10% in Triethyl citrate | 10.000 | 10.000 | 10.000 | 10.000 | 10.000 | 10.000 | 10.000 |
| 4-ACETOXY-3-PENTYL-TETRAHYDRO-PYRANE | 20.000 | 20.000 | 20.000 | 20.000 | 20.000 | 20.000 | 20.000 |
| LINALOOL | 60.000 | 60.000 | 60.000 | 60.000 | 60.000 | 60.000 | 60.000 |
| LINALYL ACETATE | 90.000 | 90.000 | 90.000 | 90.000 | 90.000 | 90.000 | 90.000 |
| ORANGE OIL BRASIL | 10.000 | 10.000 | 10.000 | 10.000 | 10.000 | 10.000 | 10.000 |

-continued

| component | example 2 Parts by weight | example 3 Parts by weight | example 4 Parts by weight | example 5 Parts by weight | example 6 Parts by weight | example 7 Parts by weight | example 8 Parts by weight |
|---|---|---|---|---|---|---|---|
| PATCHOULI OIL DECOL. | 10.000 | 10.000 | 10.000 | 10.000 | 10.000 | 10.000 | 10.000 |
| PEPPER BLACK OIL 10% in Isopropyl myristrate | 20.000 | 20.000 | 20.000 | 20.000 | 20.000 | 20.000 | 20.000 |
| PHENYLETHYL ALCOHOL | 5.000 | 5.000 | 5.000 | 5.000 | 5.000 | 5.000 | 5.000 |
| 2-ETHYL-4-(2,2,3-TRIMETHYL-3-CYCLOPENTEN-1-YL)-2-BUTEN-1-OL | 45.000 | 45.000 | 45.000 | 45.000 | 45.000 | 45.000 | 45.000 |
| TERPINEOL | 5.000 | 5.000 | 5.000 | 5.000 | 5.000 | 5.000 | 5.000 |
| VANILLIN | 5.000 | 5.000 | 5.000 | 5.000 | 5.000 | 5.000 | 5.000 |
| VERTOCITRAL | 5.000 | 5.000 | 5.000 | 5.000 | 5.000 | 5.000 | 5.000 |
| YLANG YLANG OIL | 2.500 | 2.500 | 2.500 | 2.500 | 2.500 | 2.500 | 2.500 |
| SPIRO (1.3-DIOXOLANE-2.8 (5H)-(2H-2.4A)-METHANO-NAPHTALENE)-HEXAHYDRO-1.1,5.5-TETRAMETHYL-(2S(2.ALPHA,4A.ALPHA,8A.ALPHA)) | 5.000 | 5.000 | 5.000 | 5.000 | 5.000 | 5.000 | 5.000 |
| p-tert.-butyl-alpha-methyldihydrocinnamaldehyde | 100.000 | 0.000 | 0.000 | 0.000 | 0.000 | 0.000 | 0.000 |
| 2,2-dimethyl-3-(3-methylphenyl)-propanol (component a) of the mixture of the present invention) | 0.000 | 53.400 | 53.400 | 53.400 | 53.400 | 53.400 | 53.400 |
| 4,4a,5,9b-tetrahydro-2,4-dimethylindenol[1,2-d]-m-dioxin (component b) of the mixture of the present invention) | 0.000 | 7.500 | 7.500 | 7.500 | 7.500 | 7.500 | 7.500 |
| 2-isobutyl-4-methyltetra-hydro2H-pyran-4-ol (component c) of the mixture of the present invention) | 0.000 | 0.000 | 9.300 | 9.300 | 9.300 | 9.300 | 9.300 |
| Citronellyloxyacetaldehyde (component d) of the mixture of the present invention) 50% in Dipropylene glycol | 0.000 | 0.000 | 0.000 | 0.500 | 0.500 | 0.500 | 0.500 |
| 4-n-decylpyridine (component e) of the mixture of the present invention) 1% in Triethyl citrate | 0.000 | 0.000 | 0.000 | 0.000 | 1.200 | 1.200 | 1.200 |
| 4-(4-methyl-3-penten-1-yl)-3-cyclohexene carboxaldehyde (component f) of the mixture of the present invention) | 0.000 | 0.000 | 0.000 | 0.000 | 0.000 | 27.700 | 27.700 |
| Cabreuva oil | 0.000 | 0.000 | 0.000 | 0.000 | 0.000 | 0.000 | 0.500 |

Example 2 is a comparative example. The perfume oils of examples 3 to 8 are fragrance compositions according to the present invention since each of these perfume oils comprises a fragrance mixture according to the invention. More specifically, the perfume oil of example 3 comprises a fragrance mixture according to the above-defined first preferred fragrance mixture of the invention, the perfume oil of example 4 comprises a fragrance mixture according to the above-defined second preferred fragrance mixture of the invention, the perfume oil of example 5 comprises a fragrance mixture according to the above-defined fourth preferred fragrance mixture of the invention, the perfume oil of example 6 comprises a fragrance mixture according to the above-defined fifth preferred fragrance mixture of the invention, the perfume oils of examples 7 and 8 each comprise a fragrance mixture according to the above-defined sixth preferred fragrance mixture of the invention.

Examples 9.1-9.16

Formulation Examples of Fragrance Compositions and Perfumed Products

Example 9.1

Washing Powder

| component | Function | wt % |
|---|---|---|
| Sodium metasilicate pentahydrate | | 48.0 |
| Sodium hydrogen carbonate | Alkali | 15.0 |
| Sodium carbonate peroxyhydrate | Bleaching agent | 15.0 |
| Tetraacetylethylenediamine/Na-carboxy-methylcellulose | Activator | 5.0 |
| Oxo-alcohol C14-15, 8EO | Nonionic surfactant | 3.0 |
| Sodium lauryl sulfate C12 | Anionic surfactant | 7.0 |
| Timopal CBS-X | Brightener | 0.5 |
| Protease | Enzyme | 0.4 |
| Alpha-amylase | Enzyme | 0.3 |
| Sodium sulfate | Filler | 5.5 |
| Perfume oil example 7 | Perfume (fragrance) | 0.3 |

Example 9.2

Soap

| component | Function | wt % |
|---|---|---|
| Deionized water | Solvent | 2.0 |
| Sodium tallowates/palmitates | Surfactants | 95.8 |
| Titanium dioxide | Colorant/Brightener | 1.0 |
| Perfume oil example 3 or 6 | Perfume (Fragrance) | 1.2 |

Example 9.3

All-Purpose Cleaner

| component | Function | wt % |
|---|---|---|
| Water | Solvent | ad 100 |
| 5-chloro-2-methyl-3-(2H)-isothiazolone and 2-methyl-3-(2H)-isothiazolone | Preservative | 0.1 |
| Trisodium citrate dihydrate | Chelating agent | 3.0 |
| Fatty alcohol C12-14-sulfate, sodium | Anionic surfactant | 30.0 |
| Fatty alcohol C12-C15, 8EO | Nonionic surfactant | 5.0 |
| Ethanol | Solvent | 2.0 |
| Perfume oil example 8 | Perfume (Fragrance) | 0.3 |

Example 9.4

Shampoo

| component | wt % |
|---|---|
| Deionized Water | 71.5 |
| Sodium laureth sulfate, lauryl glucoside | 20.0 |
| Glycol distearate, sodium lauryl sulfate, cocamide monoethanolamine, Laureth-10 | 6.0 |
| Phenoxyethanol, methylparaben, ethylparaben, butylparaben, propylparaben, isobutylparaben | 0.5 |
| Sodium chloride | 1.40 |
| Citric acid | 0.1 |
| Perfume oil example 8 | 0.5 |

Example 9.5

Shower Gel

| component | wt % |
|---|---|
| Deionized Water | 76.3 |
| Sodium laureth sulfate, lauryl glucoside | 20.0 |
| Phenoxyethanol, methylparaben, ethylparaben, butylparaben, propylparaben, isobutylparaben | 0.5 |
| Sodium chloride | 1.4 |
| Citric acid | 1.3 |
| Perfume (Fragrance) | 0.5 |

Example 9.6

Fine Fragrance

A fine fragrance is obtained by mixing 12 wt.-% perfume oil of example 8 and 88 wt.-% ethanol.

Example 9.7

Fabric Conditioner

| Component | Function | wt.-% |
|---|---|---|
| Water | Solvent | 72.2 |
| Dialkyl ester ammonium ethosulfate | Cationic surfactant | 16.6 |
| 5-chloro-2-methyl-3-(2H)-isothiazolone and 2-methyl-3-(2H)-isothiazolone | Preservative | 0.1 |
| Polydimethyl-siloxane | Defoamer | 0.3 |
| Magnesium chloride 1% solution in water | Thickener | 10.0 |
| Perfume oil example 8 | Perfume (fragrance) | 0.8 |

Example 9.8

Transparent Deodorant Sticks (Formulations A, B) or Deodorant Cream Sticks (Formulations C, D)

| Components | A wt.-% | B wt.-% | C wt.-% | D wt.-% |
|---|---|---|---|---|
| Aluminum zirconium tetrachlorohydrate - glycine complex | 25.00 | 20.00 | 25.00 | 20.00 |
| Dimethicone (10 cSt) | — | — | 5.00 | 5.00 |
| Cyclopentasiloxane | — | 0.50 | 1.00 | 0.50 |
| Petrolatum | 5.00 | 4.70 | 5.00 | 5.00 |
| Ozocerite | 1.00 | 1.50 | — | — |
| Stearyl alcohol | 12.00 | 12.00 | — | — |
| 2-butyloctanic acid | 0.50 | — | 0.50 | — |
| Wax | — | — | 1.25 | 1.25 |
| PPG-14 butyl ether | 9.00 | 9.00 | — | — |
| Hardened rapeseed oil | — | — | 5.00 | 5.00 |
| Silicon dioxide | — | — | 1.00 | — |
| Farnesol | 0.25 | — | 0.25 | — |
| Paraffin oil | 0.50 | 0.50 | — | — |
| Hydrogenated castor oil (castor wax) | 3.50 | 3.50 | — | — |
| Talc | 4.00 | 4.00 | — | — |
| Behenyl alcohol | 0.20 | 0.20 | — | — |
| d-Panthenyl triacetate | 1.00 | 1.00 | — | — |
| Preservative | q.s. | q.s. | q.s. | q.s. |
| Perfume oil example 7 | 1.50 | — | 1.15 | — |
| Perfume oil example 8 | — | 0.90 | — | 1.00 |
| Water | To 100 | To 100 | To 100 | To 100 |

PPG: Polypropylene glycol

Example 9.9

Antiperspirant Roll-On

| Components | wt.-% |
|---|---|
| Caprylyl trimethicone | 0.3 |
| Steareth-20 | 3.0 |
| Steareth-2 | 1.5 |
| Dicaprylyl ether | 2.0 |
| Coco-caprylate/caprate | 2.0 |
| Glycerine | 2.0 |

-continued

| Components | wt.-% |
|---|---|
| Glyceryl stearate | 2.0 |
| Octyl dodecanol | 1.0 |
| Stearyl alcohol | 2.5 |
| Aluminium chlorohydrate | 10.0 |
| Avocado extract *Persea gratissima* | 0.2 |
| Perfume oil example 8 | 1.0 |
| Water | To 100 |

Example 9.10

Antiperspirant Stick

| Components | wt.-% |
|---|---|
| Phenyl trimethicone | 13.50 |
| Cetearyl alcohol | To 100 |
| Cetiol CC (dicaprylyl carbonate) | 13.50 |
| Stearic acid | 3.50 |
| PEG-40 hydrogenated castor oil | 4.10 |
| PEG-8 distearate | 4.10 |
| Petrolatum | 6.90 |
| Aluminum chlorohydrate | 13.80 |
| Aluminium zirconium trichlorohydrex Gly | 19.50 |
| Ethylhexyl glycerine (octoxy glycerine) | 0.30 |
| 4-methyl-4-phenyl-2-pentanol | 0.25 |
| Perfume oil example 8 | 1.00 |

Example 9.11

Aerosol Spray

| Components | wt.-% |
|---|---|
| Octyldodecanol | 0.50 |
| Phenoxyethanol | — |
| 1,2-pentanediol | 1.00 |
| 1,2-hexanediol | 0.25 |
| 1,2-octanediol | 0.25 |
| Farnesol | — |
| Ethylhexyl glycerine (octoxy glycerine) | 0.50 |
| Perfume oil example 8 | 1.00 |
| Ethanol | To 100 |

The mixture obtained after mixing together the components indicated was filled into an aerosol container with a propane-butane mixture (2:7) in a ratio by weight of 2:3.

Example 9.12

O/W Lotion

| Components | wt.-% |
|---|---|
| Paraffin oil | 5.00 |
| Isopropyl palmitate | 5.00 |
| Cetyl alcohol | 2.00 |
| Beeswax | 2.00 |
| Ceteareth-20 | 2.00 |
| PEG-20-glyceryl stearate | 1.50 |
| Glycerine | 3.00 |
| Phenoxyethanol | 0.50 |

-continued

| Components | wt.-% |
|---|---|
| Parabens (mixture of methyl-, ethyl-, propyl-, butyl-, isobutylparaben) | — |
| Perfume oil example 8 | 0.30 |
| Water | To 100 |

Example 9.13

Hair Conditioner with UV Protection

| Components | wt.-% |
|---|---|
| Cetearyl alcohol | 4.00 |
| Ethylhexyl isononanoate | 4.00 |
| Potassium cetyl phosphate, hydrogenated palm glycerides | 0.50 |
| Hydroxyethylcellulose | 0.25 |
| Phenylbenzimidazole sulfonic acid | 2.00 |
| Arginine | 1.20 |
| Benzophenone-4 | 0.50 |
| Disodium phenyl dibenzimidazole tetrasulfonate | 0.50 |
| Disodium EDTA | 0.05 |
| Phenoxyethanol (and) methylparaben (and) butyparaben (and) ethyparaben (and) propylparaben | 0.80 |
| Amodimethicone, cetrimonium chloride, trideceth-12 | 2.00 |
| Laurylmethicone copolyol | 0.50 |
| Perfume oil example 8 | 0.30 |
| Water (aqua) | To 100 |

Example 9.14

Sun Protection Spray

| Part | component | wt.-% |
|---|---|---|
| A | Water (aqua) | 69.50 |
|   | Glycerine | 4.00 |
|   | Butylene glycol | 5.00 |
|   | Panthenol | 0.50 |
|   | Galactoarabinan | 0.25 |
| B | Dimethicone | 1.00 |
|   | Disodium EDTA | 0.10 |
|   | Tocopheryl acetate | 0.50 |
|   | Dicaprylyl ether | 3.00 |
|   | Homosalate | 5.00 |
|   | Ethylhexyl methoxycinnamate | 6.00 |
|   | Butyl methoxydibenzoylmethane | 1.00 |
|   | Diethylhexylnaphthalate | 2.00 |
|   | Bisabolol | 0.10 |
|   | Acrylates/C10-30 alkyl acrylate crosspolymer | 0.25 |
| C | Phenoxyethanol | 0.70 |
|   | Methylparaben | 0.20 |
|   | Propylparaben | 0.10 |
| D | Sodium hydroxide 10% in water | 0.60 |
| E | Perfume oil example 8 | 0.30 |

Production Method

Part A: Dissolve the Galactoarabinan in the other components while stirring.

Part B: Weigh in all the raw materials (except the C10-30 alkyl acrylate crosspolymer) and dissolve the crystalline substances by heating. Disperse the C10-30 alkyl acrylate crosspolymer. Add part B to part A and homogenize for 1 minute.

Parts C-E: add and homogenize for a further 1-2 minutes with the Ultra Turrax.

Example 9.15

Sun Protection Soft Cream (W/O), Sun Protection Factor (SPF) 40

| Part | component | wt.-% |
|---|---|---|
| A | Polyglyceryl-2 dipolyhydroxystearate | 5.00 |
|   | Tocopheryl acetate | 0.50 |
|   | Ozocerite | 0.50 |
|   | Zinc stearate | 0.50 |
|   | C12-15 Alkyl benzoate | 10.00 |
|   | Isoamyl-p-methoxycinnamate | 2.00 |
|   | Octocrylene | 5.00 |
|   | 4-Methylbenzylidene camphor | 3.00 |
|   | Zinc oxide | 5.00 |
| B | Water | To 100 |
|   | Disodium EDTA | 0.10 |
|   | Glycerine | 4.00 |
|   | Phenoxyethanol | 0.70 |
|   | Methylparaben | 0.20 |
|   | Propylparaben | 0.10 |
|   | Magnesium sulfate | 0.50 |
| C | Perfume oil example 8 | 0.30 |

Production Method

Part A: Heat to approximately 85° C.
Part B: Heat to approximately 85° C. (excluding zinc oxide; disperse the zinc oxide with the Ultra Turrax).
Add B to A. Allow to cool while stirring.
Part C: add and then homogenize.

Example 9.16

Sun Protection Milk (W/O)

| Part | component | wt.-% |
|---|---|---|
| A | Polyglyceryl-2 dipolyhydroxystearate | 3.00 |
|   | Beeswax | 1.00 |
|   | Glyceryl oleate | 1.00 |
|   | Zinc stearate | 1.00 |
|   | Cetearyl isononanoate | 5.00 |
|   | Dicaprylyl ether | 5.00 |
|   | C12-15 alkyl benzoate | 4.00 |
|   | Tocopherol | 0.50 |
|   | Propylparaben | 0.10 |
|   | Ethylhexyl salicylate | 5.00 |
|   | Ethylhexyl methoxycinnamate | 7.50 |
|   | Ethylhexyl triazone | 1.50 |
| B | Water (Aqua) | To 100 |
|   | Disodium EDTA | 0.10 |
|   | Glycerine | 5.00 |
|   | Methylparaben | 0.20 |
|   | Phenoxyethanol | 0.70 |
|   | Disodium phenyl dibenzimidazole tetrasulfonate 10% solution in water, neutralized with NaOH | 15.00 |
| C | Perfume oil example 8 | 0.3 |
|   | Bisabolol | 0.10 |

Production Method:

Part A: Heat to approximately 85° C.
Part B: Heat to approximately 85° C. Add B to A. Allow to cool while stirring.
Part C: Add and then homogenize.

Examples 10.1-10.6

Diffusivity and Substantivity

The diffusivity is determined by smelling 0.5 g material in a Petri dish at a distance of 50 cm from the panelist. The dish is opened upon a signal, the time stopped and the intensity ranked on a scale from 1 to 5 at the time of the impact. Each material is evaluated three times by eight panelists. Measurements should be performed in a surrounding that excludes convection or draft. The scale for intensity is defined as follows: 1=no odor to 5=strong odor. The scale for the time of the impact is defined as follows: <10 sec=4.5, <20 sec=4, <40 sec=3.5, <60 sec=3, <80 sec=2.5, <100 sec=2, <130 sec=1, <200 sec=0.5, >200 sec=0. The values of both scales are added to give the diffusivity value.

Substantivity is determined by the following procedure: 4 sheets made from cotton (weight 40 g each, 28×28 cm) and 30 ml of fabric conditioner were placed into the drum of a washing machine (Miele Novotronic Mondia 1307. Program "Stärken-kalt" (starch-cold) is carried out and spin drying at 900 rpm. The sheets are dried in a laundry dryer Miele Softtronic T422C, program "Koch-Buntwäsche Schranktrocken+" (hot/colored laundry, dry cotton+). The scent intensity of the sheets is determined by panelists according to the following scale: 1=odorless, 2=poor, 3=moderate, 4=strong, 5=very strong, 6=excellent. The composition of the fabric conditioner is as follows:

| component | wt.-% |
|---|---|
| Deioniozed water | 72.4 |
| Dialkylesterammoniummethosulfate | 16.6 |
| 5-Chloro-2-methyl-3-(2H)-isothiazolone and 2-methyl-3-(2H)-isothiazolone | 0.1 |
| Polydimethylsiloxane | 0.3 |
| Magnesium chloride 1% solution in water | 10 |
| Fragrance mixture to be tested | 0.6 |

The composition of the tested fragrance mixtures and the results of the determination of the substantivity and diffusivity are given hereinbelow:

| Example | 10.1 | 10.2 | 10.3 | 10.4 | 10.5 | 10.6 |
|---|---|---|---|---|---|---|
| component a)/wt % | 87.746 | 76.170 | 87.389 | 75.901 | 75.888 | 54.483 |
| component b)/wt % | 12.254 | 10.638 | 12.204 | 10.600 | 10.598 | 7.609 |
| component c)/wt % | 0 | 13.192 | 0 | 13.145 | 13.143 | 9.436 |
| component d)/wt % | 0 | 0 | 0.407 | 0.354 | 0.354 | 0.254 |
| component e)/wt % | 0 | 0 | 0 | 0 | 0.017 | 0.012 |
| component f)/wt % | 0 | 0 | 0 | 0 | 0 | 28.206 |
| diffusivity | 5.5 | 5.4 | 5.7 | 6.4 | 6.4 | 6.5 |
| substantivity | 3.2 | 3.5 | 3.8 | 4.0 | 4.3 | 4.6 |

The invention claimed is:

1. A mixture comprising
    a) 2,2-dimethyl-3-(3-methylphenyl)-propanol,
    b) 4,4a,5,9b-tetrahydro-2,4-dimethylindenol[1,2-d]-m-dioxin,
    c) 2-isobutyl-4-methyltetrahydro-2H-pyran-4-ol,
    d) citronellyloxyacetaldehyde,
    e) 4-n-decylpyridine, and optionally
    f) 4-(4-methyl-3-penten-1-yl)-3-cyclohexene carboxaldehyde,
    said mixture providing an odor imitating olfactory aspects of p-tert-butyl-alpha-methyldihydrocinnamaldehyde.

2. The mixture according to claim 1, wherein the weight ratio of compound a) to compound b) is in the range of from 2.5:1 to 100:1.

3. The mixture according to claim 1 comprising or consisting of
55.98-97.8999% by weight of compound a),
1-20% by weight of compound b),
1-20% by weight of compound c),
0.1-5%, by weight of compound d),
0.0001-0.02% by weight of compound e),
based on the total amount of the mixture.

4. The mixture according to claim 1, comprising
54.98-97.8999% by weight of compound a),
1-20% by weight of compound b),
1-20% by weight of compound c),
0.1-5% by weight of compound d),
0.0001-0.02% by weight of compound e), and
0% by weight of compound f),
based on the total amount of the mixture; or
  34.98-96.8999% by weight of compound a),
  1-20% by weight of compound b),
  1-20% by weight of compound c),
  0.1-5% by weight of compound d),
  0.0001-0.02% by weight of compound e), and
  5-30% by weight of compound f),
  based on the total amount of the mixture.

5. The mixture according to claim 1, wherein
the amounts of compounds a), b), c), d) and e) and—if present f), and/or
the ratio of compounds a), b) c), d) and c) and—if present—f)
are adjusted so that the mixture provides an odor comprising a white lilac blossom aspect.

6. A fragrance composition comprising an organoleptically effective amount of a mixture according to claim 1.

7. The fragrance composition according to claim 6, wherein the composition exhibits an odor comprising a white lilac blossom aspect
  (i) resulting from and/or
  (ii) enhanced by the amount of the mixture of compounds a), b), c), d), and e) and if present, f).

8. The fragrance composition according to claim 6, wherein the composition further comprises p-tert.-butyl-alpha-methyldihydro-cinnamaldehyde, and the ratio in parts by weight of p-tert.-butyl-alpha-methyldihydrocinnamaldehyde to the total amount of the mixture of compounds a), b), c), d), and e) and if present f) is in the range of from 10:1 to 1:20.

9. A perfumed product comprising a mixture according to claim 1.

10. A perfumed product according to claim 9, wherein the product exhibits an odor comprising a white lilac blossom aspect
  (i) resulting from and/or
  (ii) enhanced by the mixture of the compounds a), b), c), d), and e) and if present f).

11. A perfumed product according to claim 9, wherein said product contains about 0.05 to 5% by weight of the mixture of compounds a), b), c), d), and e) and if present f).

12. A perfumed product according to claim 9, wherein the product comprises
  (i) no, or
  (ii) less than an organoleptically and/or toxicologically effective amount of, or (iii) less than 3% by the total weight of the perfumed product of p-tert.-butyl-alpha-methyldihydrocinnamaldehyde.

13. A method of imparting an odor to a product or enhancing an odor of a product comprising:
  adding to the product or incorporating into the product an organoleptically effective amount of a mixture according to claim 1.

14. The method according to claim 13, wherein the odor which is imparted to a product or is enhanced comprises a white lilac blossom aspect preferably a white lilac blossom and a powdery aspect
  (i) resulting from and/or
  (ii) enhanced by the mixture of the compounds a), b), c), d), and e) and if present f).

15. The method according to claim 13, wherein the product after addition or incorporation of the mixture of compounds a), b), c), d), and e) and if present f) comprises
  (i) no, or
  (ii) less than an organoleptically and/or toxicologially effective amount of or
  (iii) less than 3% by weight of p-tert.-butyl-alpha-methyldihydrocinnamaldehyde.

16. The mixture according to claim 1, wherein the weight ratio of compound a) to compound b) is in the range of from 4:1 to 17:1.

17. The fragrance composition according to claim 6, wherein the composition further comprises p-tert.-butyl-alpha-methyldihydro-cinnamaldehyde, and the ratio in parts by weight of p-tert.-butyl-alpha-methyldihydrocinnamaldehyde to the amount of the mixture is in the range of from 4:1 to 1:10.

18. A perfumed product according to claim 9, wherein said product contains about 0.1 to 2.5% by weight of the mixture.

19. A perfumed product according to claim 9, wherein said product contains about 0.15 to 1% by weight of the mixture.

20. The mixture according to claim 5, wherein
the amounts of compounds a), b) c), d) and e) and—if present f),
and/or
the ratio of compounds a), b) c), d) and e) and—if present—f),
are adjusted so that the mixture provides an odor comprising a white lilac blossom and a powdery aspect.

21. A mixture consisting essentially of
  a) 2,2-dimethyl-3-(3-methylphenyl)-propanol,
  b) 4,4a,5,9b-tetrahydro-2,4-dimethylindenol[1,2-d]-m-dioxin,
  c) 2-isobutyl-4-methyltetrahydro-2H-pyran-4-ol,
  d) citronellyloxyacetaldehyde,
  e) 4-n-decylpyridine, and
  f) 4-(4-methyl-3-penten-1-yl)-3-cyclohexene carboxaldehyde,
  said mixture providing an odor imitating olfactory aspects of p-tert-butyl-alpha-methyldihydrocinnamaldehyde.

* * * * *